(12) United States Patent
Zhang et al.

(10) Patent No.: US 12,585,342 B2
(45) Date of Patent: Mar. 24, 2026

(54) WRIST-WORN DEVICE CONTROL METHOD, RELATED SYSTEM, AND STORAGE MEDIUM

(71) Applicant: HUAWEI TECHNOLOGIES CO., LTD., Shenzhen (CN)

(72) Inventors: Nu Zhang, Shenzhen (CN); Wenhao Wu, Shenzhen (CN); Qiang Xu, Toronto (CA); Shuiping Long, Beijing (CN); Ching Szu Lin, Shenzhen (CN); Vijaya Krishna Mulpuri, Shenzhen (CN); Siju Wu, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 0 days.

(21) Appl. No.: 18/955,991

(22) Filed: Nov. 22, 2024

(65) Prior Publication Data

US 2025/0085790 A1     Mar. 13, 2025

Related U.S. Application Data

(63) Continuation of application No. PCT/CN2023/100719, filed on Jun. 16, 2023.

(30) Foreign Application Priority Data

Jun. 29, 2022   (CN) ......................... 202210749952.8
Jan. 29, 2023   (CN) ......................... 202310091556.5

(51) Int. Cl.
*G06F 3/0346*     (2013.01)
*A61B 5/00*     (2006.01)
(Continued)

(52) U.S. Cl.
CPC .......... *G06F 3/0346* (2013.01); *A61B 5/1126* (2013.01); *A61B 5/681* (2013.01);
(Continued)

(58) Field of Classification Search
None
See application file for complete search history.

(56) References Cited

U.S. PATENT DOCUMENTS 10,558,278 B2   2/2020   Bernstein et al.
10,873,798 B1   12/2020   Jackson et al.
(Continued)

FOREIGN PATENT DOCUMENTS

CN     103793075 A     5/2014
CN     106486068 A     3/2017
(Continued)

*Primary Examiner* — Parul H Gupta

(57) ABSTRACT

A wrist-worn device control method is disclosed. The method includes: collecting first motion data of a wrist-worn device, where the first motion data includes angular velocity information and acceleration information of the wrist-worn device; and identifying, based on the first motion data of the wrist-worn device, that the wrist-worn device changes from a first posture to a second posture, and playing, by the wrist-worn device, media information, where the media information is at least one of a speech message, a text message, or incoming call information that are received by the wrist-worn device, and information displayed by the wrist-worn device, and the second posture is a posture in which a hand of a user wearing the wrist-worn device is close to an ear of the user. Therefore, a message can be played without occupying two hands of the user, interaction is convenient, and user experience is good.

20 Claims, 9 Drawing Sheets

(51) Int. Cl.

| | | |
|---|---|---|
| *A61B 5/11* | (2006.01) | |
| *G06F 3/01* | (2006.01) | |
| *G06F 3/16* | (2006.01) | |

(52) U.S. Cl.

CPC ................ *G06F 3/014* (2013.01); *G06F 3/16* (2013.01); *A61B 2562/0219* (2013.01); *G06F 3/017* (2013.01)

(56) References Cited

U.S. PATENT DOCUMENTS

| | | | |
|---|---|---|---|
| 2009/0164219 A1 | 6/2009 | Yeung et al. | |
| 2012/0082013 A1 | 4/2012 | Yeung et al. | |
| 2013/0147712 A1* | 6/2013 | Zhou ..................... | G06F 3/0346 |
| | | | 345/158 |
| 2016/0027282 A1* | 1/2016 | Lee ...................... | A61N 5/0622 |
| | | | 340/573.1 |
| 2016/0029911 A1* | 2/2016 | Lee ...................... | A61B 5/0205 |
| | | | 600/407 |
| 2017/0064432 A1 | 3/2017 | Hviid et al. | |
| 2021/0169417 A1* | 6/2021 | Burton ................. | A61B 5/4857 |

FOREIGN PATENT DOCUMENTS

| | | | |
|---|---|---|---|
| CN | 107197087 A | 9/2017 | |
| CN | 109981905 A | 7/2019 | |
| CN | 111656303 A | 9/2020 | |
| WO | 2018057944 A1 | 3/2018 | |

\* cited by examiner

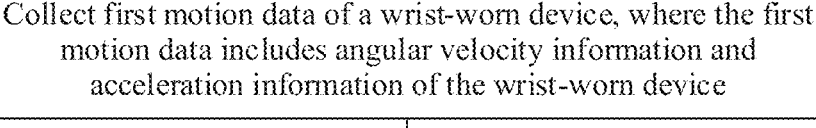

Collect first motion data of a wrist-worn device, where the first motion data includes angular velocity information and acceleration information of the wrist-worn device ⟋ 201

The wrist-worn device identifies, based on the first motion data of the wrist-worn device, that the wrist-worn device changes from a first posture to a second posture, and plays media information, where the second posture is a posture in which a hand of a user wearing the wrist-worn device is close to an ear of the user ⟋ 202

FIG. 2a

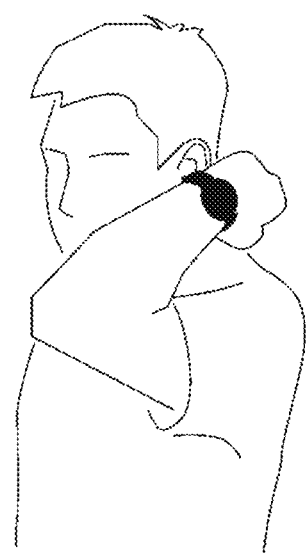

FIG. 2b

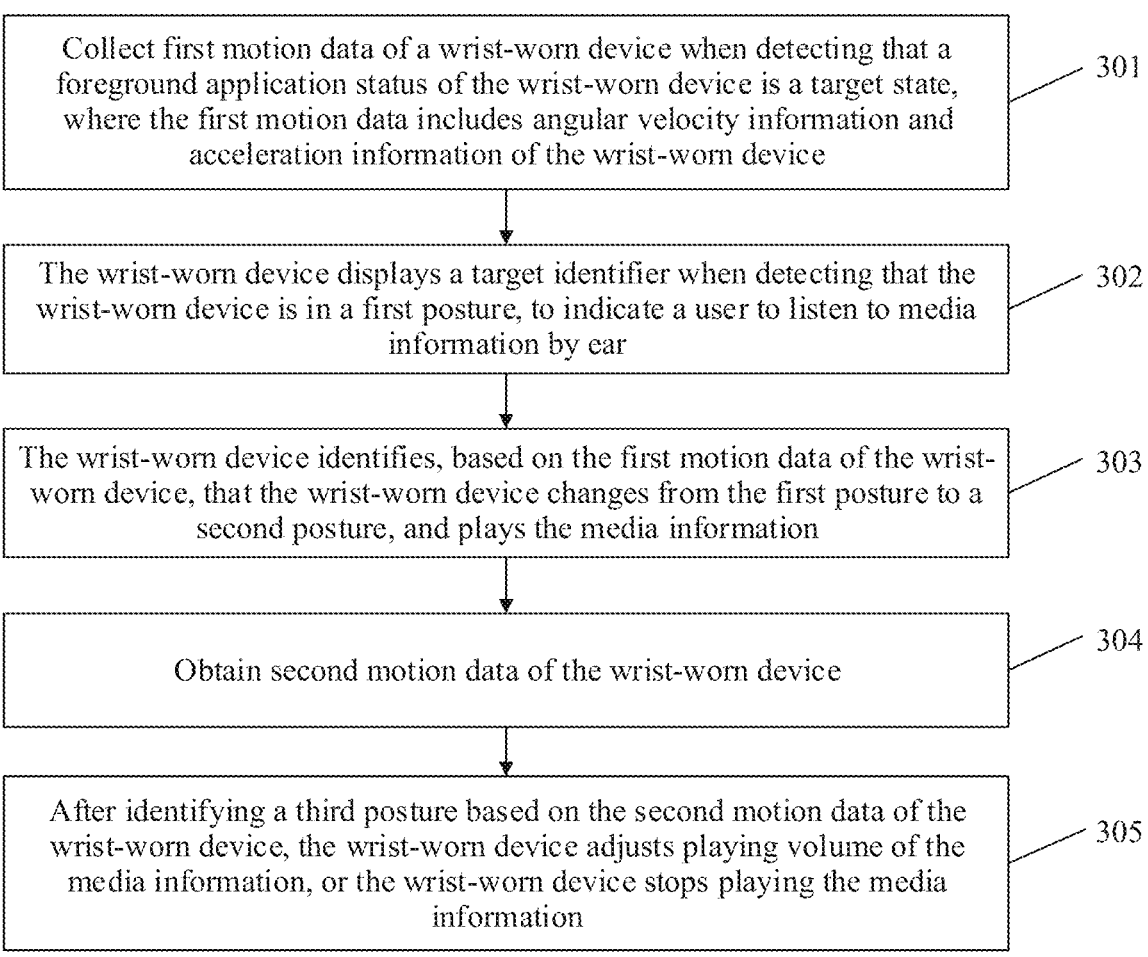

Collect first motion data of a wrist-worn device when detecting that a foreground application status of the wrist-worn device is a target state, where the first motion data includes angular velocity information and acceleration information of the wrist-worn device ⟋ 301

The wrist-worn device displays a target identifier when detecting that the wrist-worn device is in a first posture, to indicate a user to listen to media information by ear ⟋ 302

The wrist-worn device identifies, based on the first motion data of the wrist-worn device, that the wrist-worn device changes from the first posture to a second posture, and plays the media information ⟋ 303

Obtain second motion data of the wrist-worn device ⟋ 304

After identifying a third posture based on the second motion data of the wrist-worn device, the wrist-worn device adjusts playing volume of the media information, or the wrist-worn device stops playing the media information ⟋ 305

FIG. 3a

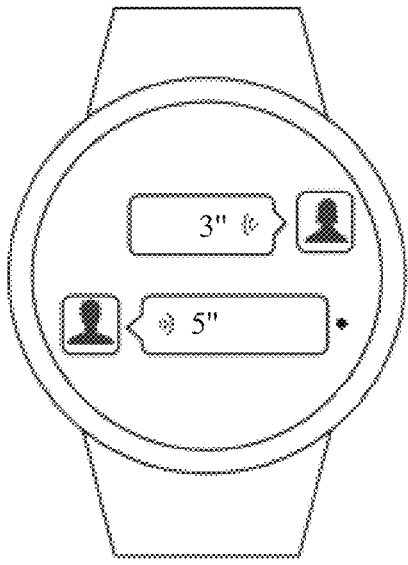

FIG. 3b xx news

News content news
content news content...

123
Heart rate (bpm)

04'55"                    2.26
Pace (/km)        Distance (km)

00:10:34
Duration

Wrist-worn device
control apparatus

Collection
module                    401

Detection
module                    402

Playing
module                    403

Wrist-worn device control apparatus 500

Memory 501              Processor 502

Bus 504

Communication
interface 503

WRIST-WORN DEVICE CONTROL METHOD, RELATED SYSTEM, AND STORAGE MEDIUM

CROSS-REFERENCE TO RELATED APPLICATIONS

This application is a continuation of International Application No. PCT/CN2023/100719, filed on Jun. 16, 2023, which claims priority to Chinese Patent Application No. 202310091556.5, filed on Jan. 29, 2023 and Chinese Patent Application No. 202210749952.8, filed on Jun. 29, 2022. All of the aforementioned patent applications are hereby incorporated by reference in their entireties.

TECHNICAL FIELD

This application relates to the field of wearable device technologies, and in particular, to a wrist-worn device control method, a related system, and a storage medium.

BACKGROUND

As a wrist-worn device (like a smartwatch or a smart band) becomes smarter, applications (Applications, Apps) may be installed and run on the wrist-worn device, for example, Apps including an audio playing function, such as social communication, a speech memo, and music, and a user may directly listen to audio on the wrist-worn device. However, when the user currently listens to the audio on the wrist-worn device, operation experience is poor.

A social communication App (for example, WeChat, QQ, or Huawei MeeTime) on a smartwatch is used as an example. When receiving a speech message, a user may choose to directly play the speech message on the watch. In a current technical solution, before playing the speech message via a loudspeaker built in the watch, the user needs to tap a button on the watch. However, from an operation perspective, tapping the button on the watch occupies two hands of the use, causing inconvenience in a scenario in which the hands are occupied (for example, carrying things, washing clothes, typing, or riding), and touching a screen with a finger may also block content on the screen.

SUMMARY

This application discloses a wrist-worn device control method, a related system, and a storage medium, to play a message without occupying two hands of a user.

According to a first aspect, an embodiment of this application provides a wrist-worn device control method, including:

collecting first motion data of a wrist-worn device, where the first motion data includes angular velocity information and acceleration information of the wrist-worn device; and identifying, based on the first motion data of the wrist-worn device, that the wrist-worn device changes from a first posture to a second posture, and playing, by the wrist-worn device, media information, where the media information is at least one of a speech message, a text message, and incoming call information that are received by the wrist-worn device, and information displayed by the wrist-worn device, where the second posture is a posture in which a hand of a user wearing the wrist-worn device is close to an ear of the user.

The first motion data may be collected in real time. After collecting the first motion data within preset time, the wrist-worn device obtains, based on the first motion data, that the wrist-worn device changes from the first posture to the second posture. For example, after collecting the first motion data within the preset time, the wrist-worn device first detects that the wrist-worn device is in the first posture at first time, and then detects that the wrist-worn device changes from the first posture to the second posture at second time. Certainly, it may alternatively be that after detecting that the wrist-worn device is in the second posture, the wrist-worn device processes the collected first motion data to detect that the wrist-worn device is in the first posture at first time, and determines that the wrist-worn device changes from the first posture to the second posture; and the like.

Alternatively, with continuous collection of the first motion data, the wrist-worn device detects in real time that the wrist-worn device is in the first posture, and then with continuous collection of the first motion data, the wrist-worn device detects that the wrist-worn device is in the second posture. Certainly, it may alternatively be that after detecting that the wrist-worn device is in the second posture, the wrist-worn device processes the collected first motion data to detect whether the wrist-worn device changes from the first posture to the second posture; or the like. A specific processing manner in which the wrist-worn device identifies the change from the first posture to the second posture is not strictly limited in this solution.

According to this embodiment of this application, the wrist-worn device obtains the first motion data of the wrist-worn device, identifies, based on the first motion data of the wrist-worn device, that the wrist-worn device changes from the first posture to the second posture, and plays the media information. This means is used. Compared with the conventional technology in which a wrist-worn device is touched and tapped by a hand to implement control, this solution is more natural and easier to learn, has higher control efficiency, frees two hands of the user, and further improves user experience.

In a possible implementation, the identifying, based on the first motion data of the wrist-worn device, that the wrist-worn device changes from a first posture to a second posture includes:

obtaining posture data and motion data based on the angular velocity information and the acceleration information of the wrist-worn device, where the posture data of the wrist-worn device includes an average pitch angle and/or an average roll angle of the wrist-worn device, and the motion data of the wrist-worn device includes a speed amplitude of the wrist-worn device, an included angle between a motion direction of the wrist-worn device and a zenith direction or a standard variance of included angles between a motion direction of the wrist-worn device and axes of an on-board east-north-up coordinate system, and at least one of data about rotation of the wrist-worn device around an x-axis, data about rotation of the wrist-worn device around a y-axis, and data about rotation of the wrist-worn device around a z-axis; and identifying, based on the posture data and the motion data, that the wrist-worn device changes from the first posture to the second posture.

In this solution, motion and posture features when the user moves a wrist close to the ear are used. This can improve accuracy of posture identification.

In a possible implementation, the identifying, based on the posture data and the motion data, that the wrist-worn device changes from the first posture to the second posture includes:

when an average pitch angle and/or an average roll angle of the wrist-worn device in the first posture fall/falls within a first preset range;

when an average pitch angle and/or an average roll angle of the wrist-worn device in the second posture fall/falls within a second preset range; and when the included angle between the motion direction of the wrist-worn device and the zenith direction falls within a third preset range or the standard variance of the included angles between the motion direction of the wrist-worn device and the axes of the on-board east-north-up coordinate system is not greater than a first preset variance, the speed amplitude of the wrist-worn device falls within a fourth preset range, and at least one of an angle in which the wrist-worn device rotates around the x-axis, an angle in which the wrist-worn device rotates around the y-axis, and an angle in which the wrist-worn device rotates around the z-axis falls within a fifth preset range, identifying that the wrist-worn device changes from the first posture to the second posture.

This means can be used to improve interaction efficiency when the user uses the wrist-worn device. The user does not need to occupy the two hands, and this avoids blocking content and reduces learning costs. In addition, in this solution, the motion and posture features when the user moves the wrist close to the ear are used. This improves accuracy of posture identification. Further, in this solution, message playing is controlled with an existing sensor IMU in the wrist-worn device. This reduces design and manufacturing costs.

In a possible implementation, the method further includes:

collecting environmental illumination data of the wrist-worn device; and the identifying, based on the first motion data of the wrist-worn device, that the wrist-worn device changes from a first posture to a second posture includes:

identifying, based on the first motion data and the environmental illumination data of the wrist-worn device, that the wrist-worn device changes from the first posture to the second posture.

It is identified, based on a combination of the collected environmental illumination data and the first motion data of the wrist-worn device, that the wrist-worn device changes from the first posture to the second posture. This comprehensively determines a posture change of the wrist-worn device from a plurality of dimensions, has more accurate control, and improves user experience.

In a possible implementation, the method further includes:

calculating an illumination reduction multiple and/or an illumination reduction value of the wrist-worn device within preset time based on the environmental illumination data; and the identifying, based on the first motion data and the environmental illumination data of the wrist-worn device, that the wrist-worn device changes from the first posture to the second posture includes:

identifying, based on the first motion data of the wrist-worn device and the illumination reduction multiple and/or the illumination reduction value of the wrist-worn device within the preset time, that the wrist-worn device changes from the first posture to the second posture.

In a possible implementation, the identifying, based on the posture data and the motion data, that the wrist-worn device changes from the first posture to the second posture includes:

when an average pitch angle and/or an average roll angle of the wrist-worn device in the first posture fall/falls within a first preset range, and the standard variance of the included angles between the motion direction of the wrist-worn device and the axes of an on-board east-north-up coordinate system is not greater than a first preset variance;

when an average pitch angle and/or an average roll angle of the wrist-worn device in the second posture fall/falls within a second preset range, and the standard variance of the included angles between the motion direction of the wrist-worn device and the axes of the on-board east-north-up coordinate system is not greater than a second preset variance; and when the included angle between the motion direction of the wrist-worn device and the zenith direction falls within a third preset range or the standard variance of the included angles between the motion direction of the wrist-worn device and the axes of the on-board east-north-up coordinate system is not greater than a third preset variance, the speed amplitude of the wrist-worn device falls within a fourth preset range, and at least one of an angle in which the wrist-worn device rotates around the x-axis, an angle in which the wrist-worn device rotates around the y-axis, and an angle in which the wrist-worn device rotates around the z-axis falls within a fifth preset range, identifying that the wrist-worn device changes from the first posture to the second posture.

In a possible implementation, the first motion data further includes light illumination change data.

The posture change of the wrist-worn device may be predicted by detecting that a light illumination change value falls within a preset change range or changes from first illumination to second illumination.

In a possible implementation, the method further includes:

generating a quaternion sequence and a relative position motion speed sequence based on the first motion data;

performing feature extraction on the quaternion sequence and the relative position motion speed sequence to obtain an extracted feature; and determining, based on the extracted feature, that the hand of the user wearing the wrist-worn device is close to the ear of the user.

Specifically, a quaternion is generated based on angular velocity data and acceleration data by using a Mahony algorithm, a Madgwick algorithm, or the like. Further, a rotation matrix is generated based on the quaternion, the acceleration data in a body coordinate system is converted into acceleration data in a geodetic coordinate system by using the rotation matrix, and gravity acceleration is eliminated. Then, a relative position motion speed is obtained through integration.

The extracted feature may include an average value, a variance, an empirical cumulative distribution function percentile, and the like.

For another example, the quaternion sequence and the relative position motion speed sequence are input into a neural network model for processing, and similarity comparison may be performed between the obtained feature (for example, a feature curve) and a preset feature, to determine that the hand of the user wearing the wrist-worn device is close to the ear of the user. Posture identification is performed in a machine learning manner. This can improve calculation efficiency.

In a possible implementation, the second posture is the posture in which the hand of the user wearing the wrist-worn device is close to the ear of the user, where the wrist-worn device is close to an ear on an opposite side of the hand of the user wearing the wrist-worn device, and a forearm of the hand of the user wearing the wrist-worn device points upward.

In another possible implementation, the second posture is the posture in which the hand of the user wearing the wrist-worn device is close to the ear of the user, where the wrist-worn device is close to an ear on a same side of the hand of the user wearing the wrist-worn device, and a forearm of the hand of the user wearing the wrist-worn device points downward, or a forearm of the hand of the user wearing the wrist-worn device is parallel to a horizontal plane.

In a possible implementation, a watch face of the wrist-worn device faces a human face or the ear.

In a possible implementation, when the wrist-worn device is in the first posture, the wrist-worn device displays a target identifier, to indicate the user to listen to the media information by ear.

Such a design is intuitive and eye-catching, and can improve user experience.

Further, when the wrist-worn device is in the first posture, the wrist-worn device determines, based on at least one of a motion status of the wrist-worn device and the environmental illumination data of the wrist-worn device, to display the target identifier, so as to indicate the user to listen to the media information by ear.

For example, when the motion status of the wrist-worn device is represented as non-intense motion and/or the environmental illumination data is higher than a preset value, the target identifier is displayed.

In a possible implementation, when identifying, based on the first motion data of the wrist-worn device, that the wrist-worn device changes from the first posture to the second posture, the wrist-worn device shields a touch control function, a knob function, or a button function. Such a design can help reduce accidental touch.

In a possible implementation, when the media information is the incoming call information received by the wrist-worn device, the method further includes:

when detecting that the wrist-worn device is in a worn state, adjusting, by the wrist-worn device, an incoming call ringing mode to a silent and vibration mode.

In other words, when the user wears the wrist-worn device, incoming call ringing is adjusted to vibration or the like. In this way, user experience is good.

In a possible implementation, when the media information is the incoming call information received by the wrist-worn device, the method further includes:

identifying, based on the first motion data and the environmental illumination data of the wrist-worn device, that the wrist-worn device changes from the first posture to the second posture, and ending, by the wrist-worn device, ringing and enabling a call mode.

In this example, when an incoming call is received, ringing may be directly ended to enter a call. This can help the user free the two hands, and the user can answer the call without touching and controlling. User experience is good.

In a possible implementation, before the playing, by the wrist-worn device, media information, the method further includes:

sending a preset message to a foreground application of the wrist-worn device or an application of the media information, to indicate the application to invoke a loudspeaker of the wrist-worn device to play the media information.

This can avoid privacy and social embarrassment problems caused by a speaker mode of the wrist-worn device.

In a possible implementation, the method further includes:

obtaining second motion data of the wrist-worn device, where the second motion data includes at least one of angular velocity information and acceleration information of the wrist-worn device; and after identifying a third posture based on the second motion data of the wrist-worn device, adjusting, by the wrist-worn device, playing volume of the media information, or stopping, by the wrist-worn device, playing the media information.

In this way, the wrist-worn device can be controlled in a plurality of manners, and user experience is good.

In a possible implementation, an operation of collecting the first motion data of the wrist-worn device is triggered when it is detected that a foreground application status of the wrist-worn device is at least one of the following:

a display interface of the wrist-worn device displays a message preview view, or the wrist-worn device is playing a message, or the wrist-worn device receives an incoming call and/or a message, or a display interface of the wrist-worn device displays a motion status monitoring view, or the wrist-worn device vibrates and/or a screen turns on.

In a possible implementation, the first posture is a posture in which the user reads on the screen.

In this solution, only an example in which the first posture is the posture in which the user reads on the screen is used for description, and the first posture may alternatively be another posture. This is not specifically limited in this solution.

In a possible implementation, the wrist-worn device plays the media information at preset volume, where the preset volume is volume for ear listening.

This means can be used to resolve privacy and social embarrassment problems caused by the speaker mode of the wrist-worn device.

According to a second aspect, an embodiment of this application provides a wrist-worn device control method, including:

collecting first motion data of a wrist-worn device, where the first motion data includes angular velocity information and acceleration information of the wrist-worn device; and identifying, based on the first motion data of the wrist-worn device, that the wrist-worn device changes from a first posture to a second posture, and playing, by the wrist-worn device, media information at first preset volume, where the media information is at least one of a speech message, a text message, and incoming call information that are received by the wrist-worn device, and information displayed by the wrist-worn device, and the first preset volume is volume for ear listening, where the second posture is a posture in which a hand of a user wearing the wrist-worn device is close to an ear of the user.

The first motion data may be collected in real time. After collecting the first motion data within preset time, the wrist-worn device obtains, based on the first motion data, that the wrist-worn device changes from the first posture to the second posture. For example, after collecting the first motion data within the preset time, the wrist-worn device first detects that the wrist-worn device is in the first posture at first time, and then detects that the wrist-worn device changes from the first posture to the second posture at second time. Certainly, it may alternatively be that after detecting that the wrist-worn device is in the second posture, the wrist-worn device processes the collected first motion data to detect that the wrist-worn device is in the first posture at first time, and determines that the wrist-worn device changes from the first posture to the second posture; and the like.

Alternatively, with continuous collection of the first motion data, the wrist-worn device detects in real time that the wrist-worn device is in the first posture, and then with continuous collection of the first motion data, the wrist-worn device detects that the wrist-worn device is in the second posture. Certainly, it may alternatively be that after detecting that the wrist-worn device is in the second posture, the wrist-worn device processes the collected first motion data to detect whether the wrist-worn device changes from the first posture to the second posture; or the like. A specific processing manner in which the wrist-worn device identifies the change from the first posture to the second posture is not strictly limited in this solution.

According to this embodiment of this application, the wrist-worn device obtains the first motion data of the wrist-worn device, identifies, based on the first motion data of the wrist-worn device, that the wrist-worn device changes from the first posture to the second posture, and plays the media information. This means is used. Compared with the conventional technology in which a wrist-worn device is touched and tapped by a hand to implement control, this solution is more natural and easier to learn, has higher control efficiency, frees two hands of the user, and further improves user experience. Playing is performed at the volume for ear listening. This can resolve privacy and social embarrassment problems caused by a speaker mode of the wrist-worn device.

Optionally, if time during which the wrist-worn device is in the first posture is less than a first threshold, the media information is played at second preset volume, where the second preset volume is not lower than the first preset volume; and/or if time during which the wrist-worn device is in the second posture is less than a second threshold, the media information is played at third preset volume, where the third preset volume is not lower than the first preset volume.

Optionally, the identifying, based on the first motion data of the wrist-worn device, that the wrist-worn device changes from a first posture to a second posture includes:

obtaining posture data and motion data based on the angular velocity information and the acceleration information of the wrist-worn device, where the posture data of the wrist-worn device includes an average pitch angle and/or an average roll angle of the wrist-worn device, and the motion data of the wrist-worn device includes a speed amplitude of the wrist-worn device, an included angle between a motion direction of the wrist-worn device and a zenith direction or a standard variance of included angles between a motion direction of the wrist-worn device and axes of an on-board east-north-up coordinate system, and at least one of data about rotation of the wrist-worn device around an x-axis, data about rotation of the wrist-worn device around a y-axis, and data about rotation of the wrist-worn device around a z-axis; and identifying, based on the posture data and the motion data, that the wrist-worn device changes from the first posture to the second posture.

Optionally, the identifying, based on the posture data and the motion data, that the wrist-worn device changes from the first posture to the second posture includes:

when an average pitch angle and/or an average roll angle of the wrist-worn device in the first posture fall/falls within a first preset range;

when an average pitch angle and/or an average roll angle of the wrist-worn device in the second posture fall/falls within a second preset range; and when the included angle between the motion direction of the wrist-worn device and the zenith direction falls within a third preset range or the standard variance of the included angles between the motion direction of the wrist-worn device and the axes of the on-board east-north-up coordinate system is not greater than a first preset variance, the speed amplitude of the wrist-worn device falls within a fourth preset range, and at least one of an angle in which the wrist-worn device rotates around the x-axis, an angle in which the wrist-worn device rotates around the y-axis, and an angle in which the wrist-worn device rotates around the z-axis falls within a fifth preset range, identifying that the wrist-worn device changes from the first posture to the second posture.

This means can be used to improve interaction efficiency when the user uses the wrist-worn device. The user does not need to occupy the two hands, and this avoids blocking content and reduces learning costs. In addition, in this solution, the motion and posture features when the user moves the wrist close to the ear are used. This improves accuracy of posture identification. Further, in this solution, message playing is controlled with an existing sensor IMU in the wrist-worn device. This reduces design and manufacturing costs.

In a possible implementation, the identifying, based on the posture data and the motion data, that the wrist-worn device changes from the first posture to the second posture includes:

when an average pitch angle and/or an average roll angle of the wrist-worn device in the first posture fall/falls within a first preset range, and the standard variance of the included angles between the motion direction of the wrist-worn device and the axes of the on-board east-north-up coordinate system is not greater than a first preset variance;

when an average pitch angle and/or an average roll angle of the wrist-worn device in the second posture fall/falls within a second preset range, and the standard variance of the included angles between the motion direction of the wrist-worn device and the axes of the on-board east-north-up coordinate system is not greater than a second preset variance; and the included angle between the motion direction of the wrist-worn device and the zenith direction falls within a third preset range or the standard variance of the included angles between the motion direction of the wrist-worn device and the axes of the on-board east-north-up coordinate system is not greater than a third preset variance, the speed amplitude of the wrist-worn device falls within a fourth preset range, and at least one of an angle in which the wrist-worn device rotates around the x-axis, an angle in which the wrist-worn device rotates around the y-axis, and an angle in which the wrist-worn device rotates around the z-axis falls within a fifth preset range, identifying that the wrist-worn device changes from the first posture to the second posture.

In a possible implementation, the method further includes:

collecting environmental illumination data of the wrist-worn device; and the identifying, based on the first motion data of the wrist-worn device, that the wrist-worn device changes from a first posture to a second posture includes:

identifying, based on the first motion data and the environmental illumination data of the wrist-worn device, that the wrist-worn device changes from the first posture to the second posture.

It is identified, based on a combination of the collected environmental illumination data and the first motion data of the wrist-worn device, that the wrist-worn device changes from the first posture to the second posture. This comprehensively determines a posture change of the wrist-worn device from a plurality of dimensions, has more accurate control, and improves user experience.

In a possible implementation, the method further includes:

generating a quaternion sequence and a relative position motion speed sequence based on the first motion data;

performing feature extraction on the quaternion sequence and the relative position motion speed sequence to obtain an extracted feature; and determining, based on the extracted feature, that the hand of the user wearing the wrist-worn device is close to the ear of the user.

In a possible implementation, the second posture is the posture in which the hand of the user wearing the wrist-worn device is close to the ear of the user, where the wrist-worn device is close to an ear on an opposite side of the hand of the user wearing the wrist-worn device, and a forearm of the hand of the user wearing the wrist-worn device points upward.

In another possible implementation, the second posture is the posture in which the hand of the user wearing the wrist-worn device is close to the ear of the user, where the wrist-worn device is close to an ear on a same side of the hand of the user wearing the wrist-worn device, and a forearm of the hand of the user wearing the wrist-worn device points downward, or a forearm of the hand of the user wearing the wrist-worn device is parallel to a horizontal plane.

In a possible implementation, a watch face of the wrist-worn device faces a human face or the ear.

In a possible implementation, when the wrist-worn device is in the first posture, the wrist-worn device displays a target identifier, to indicate the user to listen to the media information by ear.

In a possible implementation, when identifying, based on the first motion data of the wrist-worn device, that the wrist-worn device changes from the first posture to the second posture, the wrist-worn device shields a touch control function, a knob function, or a button function.

In a possible implementation, before the playing, by the wrist-worn device, media information, the method further includes:

sending a preset message to a foreground application of the wrist-worn device or an application of the media information, to indicate the application to invoke a loudspeaker of the wrist-worn device to play the media information.

In a possible implementation, the method further includes:

obtaining second motion data of the wrist-worn device, where the second motion data includes at least one of angular velocity information and acceleration information of the wrist-worn device; and after identifying a third posture based on the second motion data of the wrist-worn device, adjusting, by the wrist-worn device, playing volume of the media information, or stopping, by the wrist-worn device, playing the media information.

In a possible implementation, an operation of collecting the first motion data of the wrist-worn device is triggered when it is detected that a foreground application status of the wrist-worn device is at least one of the following:

a display interface of the wrist-worn device displays a message preview view, or the wrist-worn device is playing a message, or the wrist-worn device receives an incoming call and/or a message, or a display interface of the wrist-worn device displays a motion status monitoring view, or the wrist-worn device vibrates and/or a screen turns on.

In a possible implementation, the first posture is a posture in which the user reads on the screen.

According to a third aspect, an embodiment of this application provides a wrist-worn device control apparatus. The wrist-worn device control apparatus may include:

a collection module, configured to collect first motion data of a wrist-worn device, where the first motion data includes angular velocity information and acceleration information of the wrist-worn device;

a detection module, configured to identify, based on the first motion data of the wrist-worn device, that the wrist-worn device changes from a first posture to a second posture, where the second posture is a posture in which a hand of a user wearing the wrist-worn device is close to an ear of the user; and a playing module, configured to play media information, where the media information is at least one of a speech message, a text message, and incoming call information that are received by the wrist-worn device, and information displayed by the wrist-worn device.

In a possible implementation, the detection module is configured to:

obtain posture data and motion data based on the angular velocity information and the acceleration information of the wrist-worn device, where the posture data of the wrist-worn device includes an average pitch angle and/or an average roll angle of the wrist-worn device, and the motion data of the wrist-worn device includes a speed amplitude of the wrist-worn device, an included angle between a motion direction of the wrist-worn device and a zenith direction or a standard variance of included angles between a motion direction of the wrist-worn device and axes of an on-board east-north-up coordinate system, and at least one of data about rotation of the wrist-worn device around an x-axis, data about rotation of the wrist-worn device around a y-axis, and data about rotation of the wrist-worn device around a z-axis; and identify, based on the posture data and the motion data, that the wrist-worn device changes from the first posture to the second posture.

In a possible implementation, the detection module is further configured to:

when an average pitch angle and/or an average roll angle of the wrist-worn device in the first posture fall/falls within a first preset range;

when an average pitch angle and/or an average roll angle of the wrist-worn device in the second posture fall/falls within a second preset range; and when the included angle between the motion direction of the wrist-worn device and the zenith direction falls within a third preset range or the standard variance of the included angles between the motion direction of the wrist-worn device and the axes of the on-board east-north-up coordinate system is not greater than a first preset variance, the speed amplitude of the wrist-worn device falls within a fourth preset range, and at least one of an angle in which the wrist-worn device rotates around the x-axis, an angle in which the wrist-worn device rotates around the y-axis, and an angle in which the wrist-worn device rotates around the z-axis falls within a fifth preset range, identify that the wrist-worn device changes from the first posture to the second posture.

In a possible implementation, the collection module is further configured to:

collect environmental illumination data of the wrist-worn device; and the detection module is further configured to:

identify, based on the first motion data and the environmental illumination data of the wrist-worn device, that the wrist-worn device changes from the first posture to the second posture.

In a possible implementation, the detection module is further configured to:

calculate an illumination reduction multiple and/or an illumination reduction value of the wrist-worn device within preset time based on the environmental illumination data; and identify, based on the first motion data of the wrist-worn device and the illumination reduction multiple and/or the illumination reduction value of the wrist-worn device within the preset time, that the wrist-worn device changes from the first posture to the second posture.

In a possible implementation, the detection module is configured to:

generate a quaternion sequence and a relative position motion speed sequence based on the first motion data;

perform feature extraction on the quaternion sequence and the relative position motion speed sequence to obtain an extracted feature; and determine, based on the extracted feature, that the hand of the user wearing the wrist-worn device is close to the ear of the user.

In a possible implementation, the detection module is configured to:

when an average pitch angle and/or an average roll angle of the wrist-worn device in the first posture fall/falls within a first preset range, and the standard variance of the included angles between the motion direction of the wrist-worn device and the axes of the on-board east-north-up coordinate system is not greater than a first preset variance;

when an average pitch angle and/or an average roll angle of the wrist-worn device in the second posture fall/falls within a second preset range, and the standard variance of the included angles between the motion direction of the wrist-worn device and the axes of the on-board east-north-up coordinate system is not greater than a second preset variance; and when the included angle between the motion direction of the wrist-worn device and the zenith direction falls within a third preset range or the standard variance of the included angles between the motion direction of the wrist-worn device and the axes of the on-board east-north-up coordinate system is not greater than a third preset variance, the speed amplitude of the wrist-worn device falls within a fourth preset range, and at least one of an angle in which the wrist-worn device rotates around the x-axis, an angle in which the wrist-worn device rotates around the y-axis, and an angle in which the wrist-worn device rotates around the z-axis falls within a fifth preset range, identify that the wrist-worn device changes from the first posture to the second posture.

In a possible implementation, the second posture is the posture in which the hand of the user wearing the wrist-worn device is close to the ear of the user, where the wrist-worn device is close to an ear on an opposite side of the hand of the user wearing the wrist-worn device, and a forearm of the hand of the user wearing the wrist-worn device points upward.

In a possible implementation, the second posture is the posture in which the hand of the user wearing the wrist-worn device is close to the ear of the user, where the wrist-worn device is close to an ear on a same side of the hand of the user wearing the wrist-worn device, and a forearm of the hand of the user wearing the wrist-worn device points downward, or a forearm of the hand of the user wearing the wrist-worn device is parallel to a horizontal plane.

In a possible implementation, a watch face of the wrist-worn device faces a human face or the ear.

In a possible implementation, when the wrist-worn device is in the first posture, the wrist-worn device control apparatus determines, based on at least one of a motion status of the wrist-worn device and the environmental illumination data of the wrist-worn device, to display the target identifier, so as to indicate the user to listen to the media information by ear.

In a possible implementation, when identifying, based on the first motion data of the wrist-worn device, that the wrist-worn device changes from the first posture to the second posture, the wrist-worn device control apparatus shields a touch control function, a knob function, or a button function of the wrist-worn device.

In a possible implementation, when the media information is the incoming call information received by the wrist-worn device, the playing module is further configured to:

when it is detected that the wrist-worn device is in a worn state, adjust an incoming call ringing mode to a silent and vibration mode.

In a possible implementation, when the media information is the incoming call information received by the wrist-worn device, the playing module is further configured to:

identify, based on the first motion data and the environmental illumination data of the wrist-worn device, that the wrist-worn device changes from the first posture to the second posture, end ringing, and enable a call mode.

In a possible implementation, before the wrist-worn device plays the media information, the apparatus further includes a sending module, configured to:

send a preset message to a foreground application of the wrist-worn device or an application of the media information, to indicate the application to invoke a loudspeaker of the wrist-worn device to play the media information.

In a possible implementation, the collection module is further configured to:

obtain second motion data of the wrist-worn device, where the second motion data includes at least one of angular velocity information and acceleration information of the wrist-worn device;

the detection module is further configured to identify a third posture based on the second motion data of the wrist-worn device; and the playing module is further configured to: adjust playing volume of the media information, or stop playing the media information.

In a possible implementation, the collection module is triggered to collect the first motion data of the wrist-worn device when the detection module detects that a foreground application status of the wrist-worn device is at least one of the following:

a display interface of the wrist-worn device displays a message preview view, or the wrist-worn device is playing a message, or the wrist-worn device receives an incoming call and/or a message, or a display interface of the wrist-worn device displays a motion status monitoring view, or the wrist-worn device vibrates and/or a screen turns on.

In a possible implementation, the first posture is a posture in which the user reads on the screen.

In a possible implementation, the playing module is configured to play the media information at preset volume, where the preset volume is volume for ear listening.

According to a fourth aspect, an embodiment of this application provides a wrist-worn device control apparatus. The wrist-worn device control apparatus may include a collection module, a detection module, and a playing module, which are specifically described in the following.

The collection module is configured to collect first motion data of a wrist-worn device, where the first motion data includes angular velocity information and acceleration information of the wrist-worn device.

The detection module is configured to identify, based on the first motion data of the wrist-worn device, that the wrist-worn device changes from a first posture to a second posture, where the second posture is a posture in which a hand of a user wearing the wrist-worn device is close to an ear of the user.

The playing module is configured to play media information at first preset volume, where the media information is at least one of a speech message, a text message, and incoming call information that are received by the wrist-worn device, and information displayed by the wrist-worn device, and the first preset volume is volume for ear listening.

Optionally, if time during which the wrist-worn device is in the first posture is less than a first threshold, the playing module is configured to play the media information at second preset volume, where the second preset volume is not lower than the first preset volume; and/or if time during which the wrist-worn device is in the second posture is less than a second threshold, the playing module is configured to play the media information at third preset volume, where the third preset volume is not lower than the first preset volume.

Optionally, the detection module is configured to:

obtain posture data and motion data based on the angular velocity information and the acceleration information of the wrist-worn device, where the posture data of the wrist-worn device includes an average pitch angle and/or an average roll angle of the wrist-worn device, and the motion data of the wrist-worn device includes a speed amplitude of the wrist-worn device, an included angle between a motion direction of the wrist-worn device and a zenith direction or a standard variance of included angles between a motion direction of the wrist-worn device and axes of an on-board east-north-up coordinate system, and at least one of data about rotation of the wrist-worn device around an x-axis, data about rotation of the wrist-worn device around a y-axis, and data about rotation of the wrist-worn device around a z-axis; and identify, based on the posture data and the motion data, that the wrist-worn device changes from the first posture to the second posture.

Optionally, the detection module is further configured to:

when an average pitch angle and/or an average roll angle of the wrist-worn device in the first posture fall/falls within a first preset range;

when an average pitch angle and/or an average roll angle of the wrist-worn device in the second posture fall/falls within a second preset range; and when the included angle between the motion direction of the wrist-worn device and the zenith direction falls within a third preset range or the standard variance of the included angles between the motion direction of the wrist-worn device and the axes of the on-board east-north-up coordinate system is not greater than a first preset variance, the speed amplitude of the wrist-worn device falls within a fourth preset range, and at least one of an angle in which the wrist-worn device rotates around the x-axis, an angle in which the wrist-worn device rotates around the y-axis, and an angle in which the wrist-worn device rotates around the z-axis falls within a fifth preset range, identify that the wrist-worn device changes from the first posture to the second posture.

In a possible implementation, the collection module is further configured to:

collect environmental illumination data of the wrist-worn device; and the detection module is further configured to:

identify, based on the first motion data and the environmental illumination data of the wrist-worn device, that the wrist-worn device changes from the first posture to the second posture.

In a possible implementation, the detection module is configured to:

generate a quaternion sequence and a relative position motion speed sequence based on the first motion data;

perform feature extraction on the quaternion sequence and the relative position motion speed sequence to obtain an extracted feature; and determine, based on the extracted feature, that the hand of the user wearing the wrist-worn device is close to the ear of the user.

In a possible implementation, the second posture is the posture in which the hand of the user wearing the wrist-worn device is close to the ear of the user, where the wrist-worn device is close to an ear on an opposite side of the hand of the user wearing the wrist-worn device, and a forearm of the hand of the user wearing the wrist-worn device points upward.

In a possible implementation, the second posture is the posture in which the hand of the user wearing the wrist-worn device is close to the ear of the user, where the wrist-worn device is close to an ear on a same side of the hand of the user wearing the wrist-worn device, and a forearm of the hand of the user wearing the wrist-worn device points downward, or a forearm of the hand of the user wearing the wrist-worn device is parallel to a horizontal plane.

In a possible implementation, a watch face of the wrist-worn device faces a human face or the ear.

In a possible implementation, when the wrist-worn device is in the first posture, the wrist-worn device control apparatus displays a target identifier, to indicate the user to listen to the media information by ear.

In a possible implementation, when identifying, based on the first motion data of the wrist-worn device, that the wrist-worn device changes from the first posture to the second posture, the wrist-worn device control apparatus shields a touch control function, a knob function, or a button function of the wrist-worn device.

In a possible implementation, before the wrist-worn device plays the media information, the apparatus further includes a sending module, configured to:

send a preset message to a foreground application of the wrist-worn device or an application of the media information, to indicate the application to invoke a loudspeaker of the wrist-worn device to play the media information.

In a possible implementation, the collection module is further configured to:

obtain second motion data of the wrist-worn device, where the second motion data includes at least one of angular velocity information and acceleration information of the wrist-worn device;

the detection module is further configured to identify a third posture based on the second motion data of the wrist-worn device; and the playing module is further configured to: adjust playing volume of the media information, or stop playing the media information.

In a possible implementation, the collection module is triggered to collect the first motion data of the wrist-worn device when the detection module detects that a foreground application status of the wrist-worn device is at least one of the following:

a display interface of the wrist-worn device displays a message preview view, or the wrist-worn device is playing a message, or the wrist-worn device receives an incoming call and/or a message, or a display interface of the wrist-worn device displays a motion status monitoring view, or the wrist-worn device vibrates and/or a screen turns on.

In a possible implementation, the first posture is a posture in which the user reads on the screen.

According to a fifth aspect, this application provides a wrist-worn device control apparatus, including a processor and a memory. The memory is configured to store program code, and the processor is configured to invoke the program code, to perform the method according to any possible implementation of the first aspect and/or the method according to any possible implementation of the second aspect.

According to a sixth aspect, this application provides a computer storage medium, including computer instructions. When the computer instructions are run on an electronic device, the electronic device is enabled to perform the method according to any possible implementation of the first aspect and/or the method according to any possible implementation of the second aspect.

According to a seventh aspect, an embodiment of this application provides a computer program product. When the computer program product runs on a computer, the computer is enabled to perform the method according to any possible implementation of the first aspect and/or the method according to any possible implementation of the second aspect.

It may be understood that the wrist-worn device control apparatus according to the third aspect, the wrist-worn device control apparatus according to the fourth aspect, the wrist-worn device control apparatus according to the fifth aspect, the computer storage medium according to the sixth aspect, or the computer program product according to the seventh aspect each is configured to perform the method according to any one of the first aspect and/or the method according to any possible implementation of the second aspect. Therefore, for beneficial effect that can be achieved by the wrist-worn device control apparatus, the computer storage medium, and the computer program product, refer to the beneficial effect in the corresponding methods. Details are not described herein again.

BRIEF DESCRIPTION OF DRAWINGS

The following describes accompanying drawings in the embodiments of this application.

FIG. 2a is a schematic flowchart of a wrist-worn device control method according to an embodiment of this application;

FIG. 2b is a diagram of a gesture according to an embodiment of this application;

FIG. 3a is a schematic flowchart of another wrist-worn device control method according to an embodiment of this application;

FIG. 3b is a diagram of a wrist-worn device in a message preview view according to an embodiment of this application;

DESCRIPTION OF EMBODIMENTS

Figure 1A:
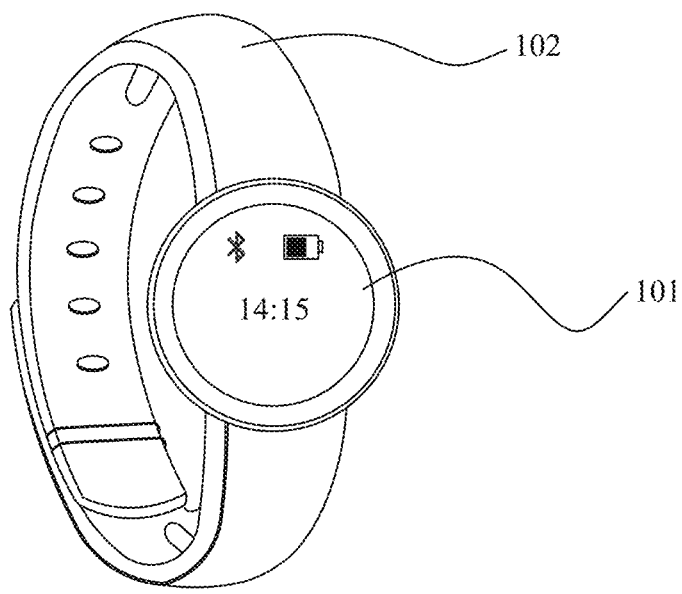
FIG. 1a is a diagram of a wrist-worn device according to an embodiment of this application.

The following describes embodiments of this application with reference to accompanying drawings in embodiments of this application. Terms used in implementations of embodiments of this application are merely used to explain specific embodiments of this application, and are not intended to limit this application.

For ease of understanding, some concepts related to embodiments of this application are described for reference by using examples below. Details are as follows.

1. Wrist-worn device: A wrist-worn device is a smart device worn on a wrist of a user. Common forms include a smartwatch and a smart band.

2. Inertial measurement unit (IMU): An inertial measurement unit is an apparatus for measuring a triaxial attitude angle (or angular rate) and acceleration of an object. Generally, the IMU is used to detect a motion status of a device, including rotation angular velocities, angles, acceleration, and device postures on three axes.

3. Proximity sensor: A proximity sensor is used to detect whether an object is approaching. Common proximity sensors include an infrared sensor, an ultrasonic sensor, a capacitive sensor, and the like.

4. On-board east-north-up (ENU) coordinate system: An on-board east-north-up coordinate system is also referred to as topocentric coordinate system. A position P of a user is used as an origin of coordinates. The coordinate system is defined by using an x-axis pointing to the east, a y-axis pointing to the north, and a z-axis pointing to the zenith.

An ENU local coordinate system describes the earth's surface by using a three-dimensional rectangular coordinate system and usually by using a simplified two-dimensional projection coordinate system. In many two-dimensional projection coordinate systems, a unified horizontal axis Mercator (The Universal Transverse Mercator, UTM) coordinate system is widely used. The UTM coordinate system represents coordinates in a grid-based method, and divides the earth into 60 longitude zones, where each zone includes a longitude range of 6 degrees, and coordinates in each zone are projected based on the horizontal axis Mercator.

5. Text-to-SpeechTTS) technology: A text-to-speech technology is a technology that converts text information generated by a device or externally input into understandable and fluent Chinese oral output.

6. Environment light sensor: An environment light sensor detects environmental illumination and light color temperature. Generally, a plurality of light sensing elements (or referred to as a plurality of channels) are included, and are sensitive to different spectra, for example, red light, blue light, blue light, white light, and near-infrared light. The sensor generally fuses output of the plurality of light sensing elements to obtain an environmental illumination value.

The foregoing example descriptions of the concepts may be applied in the following embodiments.

When a wrist-worn device receives a new message, a user needs to tap a button or the like on the device to trigger displaying or playing of the wrist-worn device. This is very inconvenient for the user. In view of this, this application provides a wrist-worn device control method, a related system, and a storage medium, to identify that the wrist-worn device changes from a first posture to a second posture, where the second posture is a posture in which a hand of a user wearing the wrist-worn device is close to an ear of the user, and play media information. This meets a requirement of the user for freeing two hands and improving user experience.

The following describes in detail the wrist-worn device in embodiments of this application with reference to the accompanying drawings. FIG. 1*a* is a diagram of a wrist-worn device to which an embodiment of this application is applicable. The wrist-worn device includes a watch face 101 and a watch band 102. The watch band 102 is used by a user to wear the wrist-worn device. The watch face 101 is configured to display time, a battery level, a message, and the like.

It should be noted that the wrist-worn device in this embodiment of this application may be a smartwatch, a smart band, or another wearable device, and this is not specifically limited in this solution.

Figure 1B:
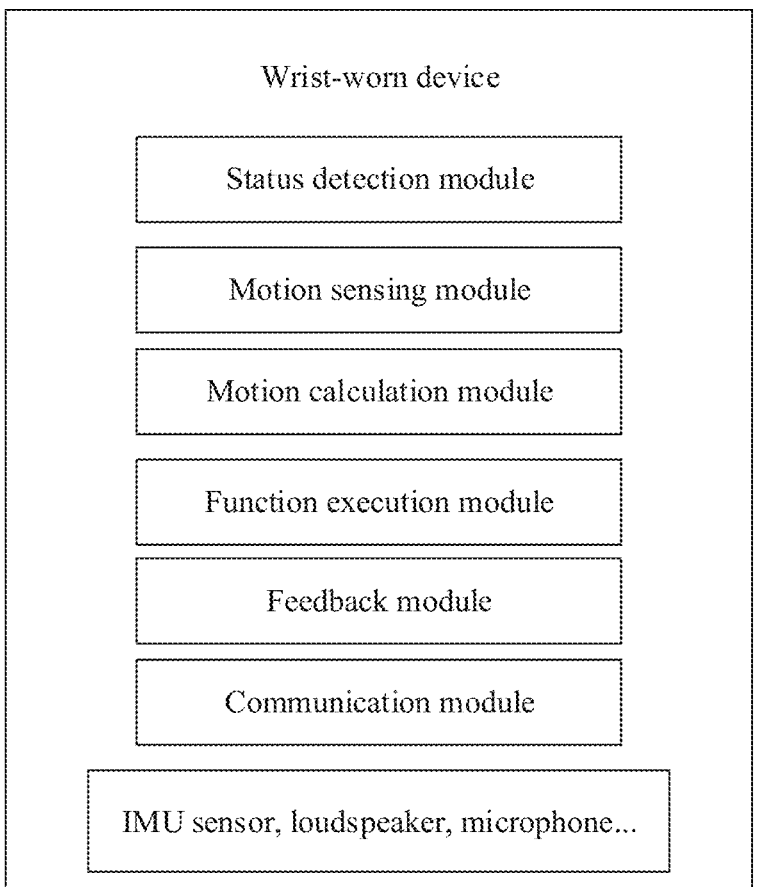
FIG. 1b is a diagram of a structure of a wrist-worn device according to an embodiment of this application.

FIG. 1*b* is a diagram of a structure of a wrist-worn device according to an embodiment of this application. As shown in FIG. 1*b*, the wrist-worn device includes a status detection module, a motion sensing module, a motion calculation module, a function execution module, a feedback module, and a communication module.

The status detection module is configured to determine a current running state of the wrist-worn device, to trigger motion sensing, motion calculation, and the like in a specific target running state.

The motion sensing module includes at least an accelerometer and a gyroscope (also referred to as an angular velocity meter), and is configured to sense and output, at a specific time interval, an acceleration value of each axial direction of the wrist-worn device and a rotation angular velocity value of rotation of the wrist-worn device around each axial direction.

The motion calculation module is configured to calculate motion data of the wrist-worn device based on output of the motion sensing module, where the motion data may include posture data (such as a pitch angle and a roll angle), position motion data (such as a motion speed amplitude and a motion direction), and posture motion data (such as an angle in which the wrist-worn device rotates around each axial direction). The motion calculation module may further identify, based on the motion data, whether a specific target motion mode exists, and indicate, if identifying the target motion mode (for example, a motion mode generated when the wrist-worn device moves to an ear in a current natural reading posture of a user), the function execution module, the feedback module, the communication module, and the like to perform corresponding operations.

The function execution module is configured to perform a specific function operation according to an indication of the motion calculation module. For example, the function execution module may be an audio processing module, or the like.

The feedback module is configured to provide feedback for the user at a specific moment according to an indication of the status detection module, the motion calculation module, or the like. For example, the feedback includes visual, auditory, and tactile feedback.

The communication module is configured to keep a wireless connection to another device, or send instructions to a paired device according to an indication of the motion calculation module, or send a message via a cellular network module in the communication module, or the like.

The wrist-worn device may further include a magnetometer, a touch control module, a watch crown knob, a watch face knob, a button, a screen, a loudspeaker, a microphone, a central processing unit (CPU), a memory, a vibration motor, and the like.

The foregoing modules are merely examples. In another embodiment, the wrist-worn device may include more modules than the foregoing modules, fewer modules than the foregoing modules, or the like. This is not strictly limited in this solution.

In a possible implementation, the wrist-worn device further includes an environmental illumination detection module. The environmental illumination detection module is configured to detect a current real-time environmental illumination value of the wrist-worn device.

Correspondingly, the feedback module is configured to provide feedback for the user at a specific moment according to an indication of the status detection module, the environmental illumination detection module, the motion calculation module, or the like. For example, the feedback includes visual, auditory, and tactile feedback.

In this solution, the motion data of the wrist-worn device is obtained, then it is identified, based on the motion data of the wrist-worn device, that the wrist-worn device changes from the first posture to the posture in which the hand of the user wearing the wrist-worn device is close to the ear of the user, and the media information is played. Compared with the conventional technology in which a wrist-worn device is touched or tapped by a hand to implement control of the wrist-worn device, this solution is more natural and easier to learn, has higher control efficiency, and further improves user experience.

Figure 1C:
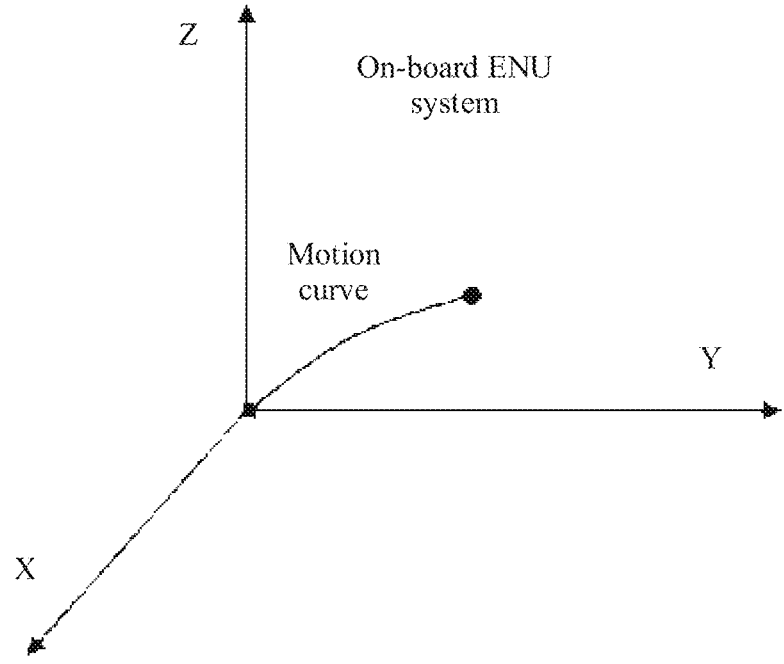
FIG. 1c is a diagram of an on-board ENU coordinate system according to an embodiment of this application.

FIG. 1c shows an on-board east-north-up (ENU) coordinate system in an embodiment of this application. In the coordinate system, a position of a user is used as an origin of coordinates, an x-axis points to the east, a y-axis points to the north, and a z-axis points to the zenith.

Figure 1D:
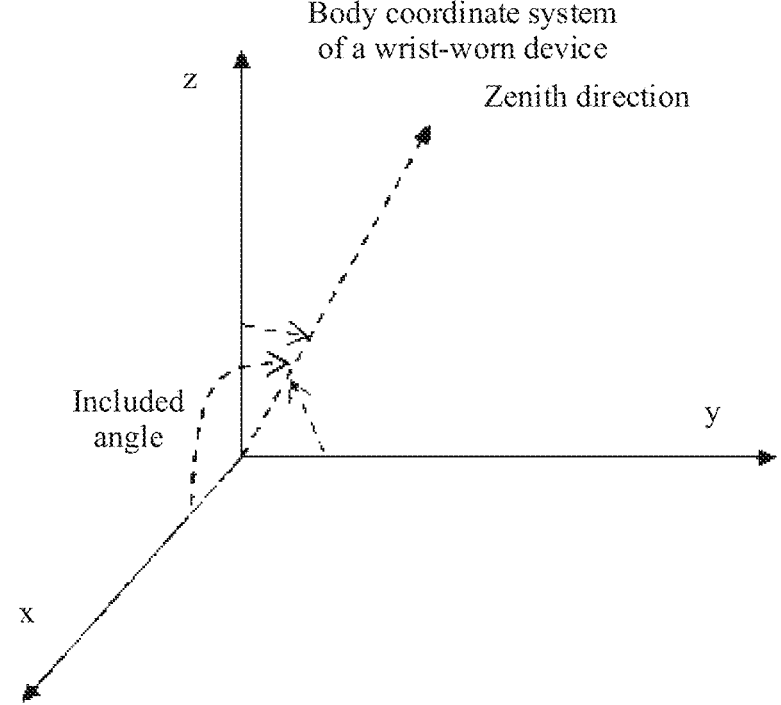
FIG. 1d is a diagram of a body coordinate system of a wrist-worn device according to an embodiment of this application.

A zenith direction in embodiments of this application may be based on a body coordinate system of the wrist-worn device. As shown in FIG. 1d, an origin of coordinates in the body coordinate system of the wrist-worn device is a watch face center of the wrist-worn device, an x-axis in the body coordinate system points from the watch face center to a direction of 3 o'clock, a y-axis in the body coordinate system points from the watch face center to a direction of 12 o'clock, and a z-axis in the body coordinate system is perpendicular to a watch face plane and points above the watch face.

The following describes in detail the method in embodiments of this application.

FIG. 2a is a schematic flowchart of a wrist-worn device control method according to an embodiment of this application. As shown in FIG. 2a, the method may include steps 201 and 202. An example in which steps 201 and 202 in the wrist-worn device control method are performed by a wrist-worn device is used below for description. This application is also applicable to another execution body. Steps 201 and 202 are specifically as follows.

201: Collect first motion data of the wrist-worn device, where the first motion data includes angular velocity information and acceleration information of the wrist-worn device.

The angular velocity information may be understood as a ratio of an angle in which the wrist-worn device rotates around an axis to time. In a possible implementation, the angular velocity information may include, for example, rotation angular velocities and angles of three axes: an x-axis, a y-axis, and a z-axis of the wrist-worn device.

The acceleration information may be understood as a ratio of a speed change amount of the wrist-worn device to time for the change, and is a physical quantity that describes a speed change speed of an object. In a possible implementation, the acceleration information may include, for example, acceleration of the three axes: the x-axis, the y-axis, and the z-axis of the wrist-worn device.

For example, the angular velocity information and the acceleration information of the wrist-worn device may be obtained with an IMU sensor in the wrist-worn device. Alternatively, the first motion data may be generated based on angular velocity meter output and accelerometer output of the wrist-worn device. Specifically, time synchronization calculation is first performed between the angular velocity meter output and the accelerometer output, and then the first motion data is generated.

In a possible implementation, the wrist-worn device may collect the first motion data in real time, or may periodically collect the first motion data, or may trigger collection of the first motion data when a preset condition is met. This is not specifically limited in this solution.

It should be noted that this embodiment of this application is described by using an example in which the first motion data includes the angular velocity information and the acceleration information of the wrist-worn device. In another embodiment, the first motion data may further include one or more of a rotation angle, a speed, displacement, gravity acceleration, posture data, vectors of the x-axis, the y-axis, and the z-axis of the wrist-worn device in a world geodetic system, and the like. Optionally, the first motion data may further include light illumination change data. For example, a posture change of the wrist-worn device may be predicted with assistance by detecting that a light illumination change value falls within a preset change range or changes from first illumination to second illumination. The foregoing is merely an example, and this is not specifically limited in this solution.

202: The wrist-worn device identifies, based on the first motion data of the wrist-worn device, that the wrist-worn device changes from a first posture to a second posture, and plays media information, where the second posture is a posture in which a hand of a user wearing the wrist-worn device is close to an ear of the user, the media information is at least one of a speech message, a text message, and incoming call information that are received by the wrist-worn device, and information displayed by the wrist-worn device.

The first posture may be a posture in which the user reads on a screen, for example, may be a posture in which the user raises a hand to read on the watch face screen of the wrist-worn device. Certainly, the first posture may alternatively be another posture, for example, may be a posture in which the user naturally hangs down the hand wearing the wrist-worn device. The first posture may alternatively be another posture. This is not specifically limited in this solution.

The second posture may be the posture in which the hand of the user wearing the wrist-worn device is close to the ear of the user, for example, may be a posture in which the hand of the user wearing the wrist-worn device is close to the ear of the user. FIG. 2b is a diagram of wearing a wrist-worn device by a user. FIG. 2b shows a posture in which a hand of the user wearing the wrist-worn device is close to an ear of the user. In this example, the wrist-worn device is close to an ear on a same side of the hand of the user wearing the wrist-worn device. For example, a left hand corresponds to a left ear. In addition, a forearm of the hand of the user wearing the wrist-worn device points upward (including that the forearm of the hand of the user wearing the wrist-worn device is parallel to a horizontal plane). A watch face of the wrist-worn device faces a human face, the ear, or the like.

Figure 2C:
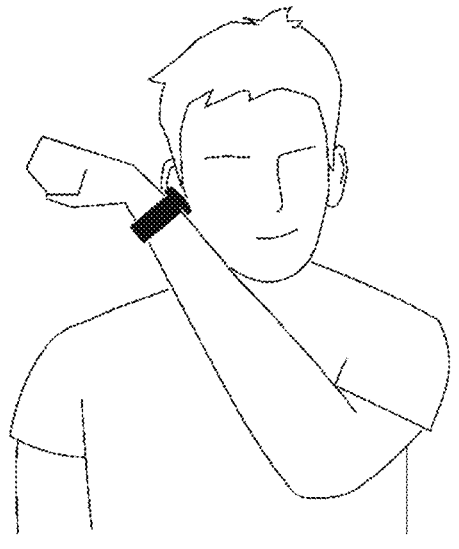
FIG. 2c is a diagram of another gesture according to an embodiment of this application.

FIG. 2c is another diagram of wearing a wrist-worn device by a user. FIG. 2c also shows a posture in which a hand of the user wearing the wrist-worn device is close to an ear of the user. In this example, the wrist-worn device is close to an ear on an opposite side of the hand of the user wearing the wrist-worn device. For example, a left hand corresponds to a right ear. In addition, a forearm of the hand of the user wearing the wrist-worn device points upward. A watch face of the wrist-worn device faces a human face, the ear, or the like.

Figure 2D:
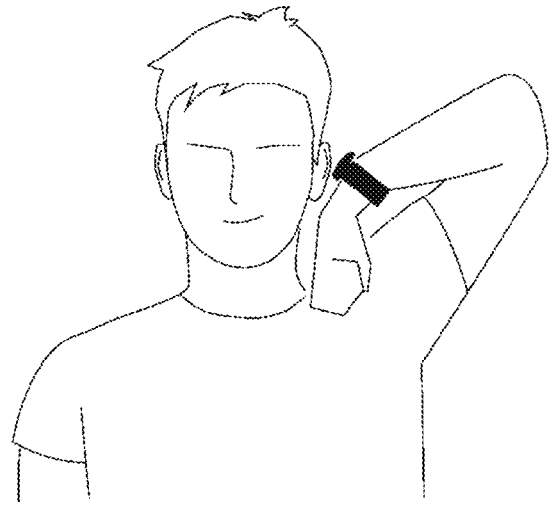
FIG. 2d is a diagram of still another gesture according to an embodiment of this application.

FIG. 2d is still another diagram of wearing a wrist-worn device by a user. FIG. 2d also shows a posture in which a hand of the user wearing the wrist-worn device is close to an ear of the user. In this example, the wrist-worn device is close to an ear on a same side of the hand of the user wearing the wrist-worn device. For example, a left hand corresponds to a left ear. In addition, a forearm of the hand of the user wearing the wrist-worn device points downward (including that the forearm of the hand of the user wearing the wrist-worn device is parallel to a horizontal plane). A watch face of the wrist-worn device faces a human face, the ear, or the like.

The postures shown in FIG. 2b, FIG. 2c, and FIG. 2d are merely examples, and may alternatively be other postures. This is not specifically limited in this solution.

The media information may be one or more of the speech message, the text message, and the incoming call information that are received by the wrist-worn device, the information displayed by the wrist-worn device, and the like.

The speech message received by the wrist-worn device may be, for example, a speech message received by a chat application (App) or the like installed on the wrist-worn device, or may be another speech message. This is not specifically limited in this solution.

The text message may be, for example, one or more of an SMS message or a notification pushed by an App.

The incoming call information may be, for example, incoming call information received by the wrist-worn device from a paired mobile phone, or call information received by a chat application or the like installed on the wrist-worn device, or incoming call information corresponding to a call function built in the wrist-worn device.

The information displayed by the wrist-worn device may be, for example, time information or text information.

The media information is described above. Manners of identifying that the wrist-worn device changes from the first posture to the second posture are described below.

Manner 1: Obtain posture data and motion data based on the angular velocity information and the acceleration information of the wrist-worn device, and identify, based on the posture data and the motion data, that the wrist-worn device changes from the first posture to the second posture.

The posture data of the wrist-worn device includes one or more of a pitch angle, a roll angle, or the like.

The motion data of the wrist-worn device may include posture motion data and position motion data.

Figure 2E:
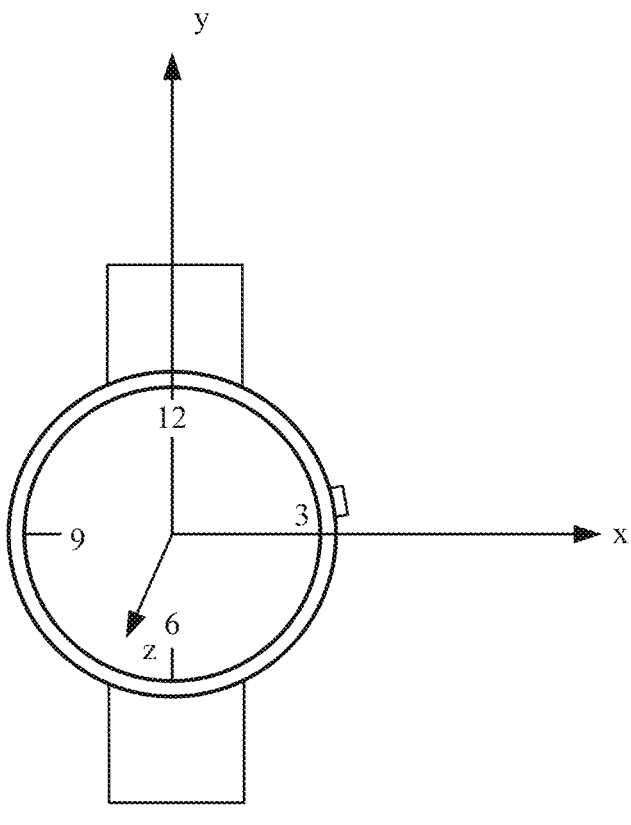
FIG. 2e is a diagram of each axis of a smartwatch according to an embodiment of this application.

In a possible implementation, the posture motion data includes one or more of data about rotation of the wrist-worn device around an x-axis, data about rotation of the wrist-worn device around a y-axis, and data about rotation of the wrist-worn device around a z-axis, and the like. Optionally, FIG. 2e is a diagram of each axis in a top view of a smartwatch according to an embodiment of this application. The smartwatch is used as an example. An x-axis in the smartwatch points from a watch face center to a direction of 3 o'clock, a y-axis in the smartwatch points from the watch face center to a direction of 12 o'clock, and a z-axis in the smartwatch is perpendicular to a watch face plane and points above a watch face. Certainly, another coordinate system, another relative position limitation, or the like may be used. For example, an x-axis is located in a direction in which a center of the wrist-worn device points to 6 o'clock, a y-axis is located in a direction in which the center of the wrist-worn device points to 3 o'clock, and a z-axis is perpendicular to a plane on which the wrist-worn device is located, points to above the plane, and the like. This is not specifically limited in this solution.

The position motion data includes one or more of a speed amplitude, motion direction data, or the like. The motion direction data includes one or more of an included angle between a motion direction of the wrist-worn device and a zenith direction, a standard variance of components of a motion direction of the wrist-worn device on axes of an on-board east-north-up (ENU) coordinate system, or the like.

It may be understood that, optionally, the first motion data includes posture data of the wrist-worn device in the first posture (for example, a current natural reading posture), posture data of the wrist-worn device in the second posture (a posture after the wrist-worn device moves to the ear), and motion data (position motion data and posture motion data) in a process in which the wrist-worn device changes from the first posture to the second posture (from the current natural reading posture to the posture moving to the ear).

It should be noted that the posture data and the motion data are merely examples, and may further include other data. This is not specifically limited in this solution.

In a possible implementation, the posture data and the motion data are obtained based on the angular velocity information and the acceleration information of the wrist-worn device.

For example, an average pitch angle and/or an average roll angle of the wrist-worn device are/is obtained based on the acceleration information in the first motion data. Specifically, $tmp=sqrt(ay*ay+az*az)$, pitch (pitch angle)$=-atan\ 2(ax, tmp)$, and roll (roll angle)$=atan\ 2(ay, az)$. A symbol of the pitch angle is the same as a (positive or negative) symbol of az, ay is acceleration of the wrist-worn device on the y-axis, az is acceleration of the wrist-worn device on the z-axis, and ax is acceleration of the wrist-worn device on the x-axis.

That the wrist-worn device is in the first posture or the wrist-worn device is in the second posture is determined based on comparison between the average pitch angle and/or the average roll angle and a preset value.

For another example, a quaternion is generated based on the angular velocity information and the acceleration information by using a Mahony algorithm, a Madgwick algorithm, or the like. Further, a rotation matrix is generated based on the quaternion, acceleration data in a body coordinate system is converted into acceleration data in a geodetic coordinate system by using the rotation matrix, and gravity acceleration is eliminated. Then, a relative position motion speed is obtained through integration. The included angle between the motion direction of the wrist-worn device and the zenith direction can be obtained through calculation by calculating an included angle between a motion speed vector and a zenith direction vector [0, 0, 1].

For another example, included angles between the motion direction of the wrist-worn device and the axes of an on-board east-north-up coordinate system are solved, and then the standard variance is calculated based on an included angle sequence, that is, the standard variance of the included angles between the motion direction of the wrist-worn device and the axes of an on-board east-north-up coordinate system is obtained. For a manner of solving the angles, refer to the foregoing descriptions. Details are not described herein again.

For another example, a quaternion is generated based on the angular velocity information and the acceleration information by using a Mahony algorithm, a Madgwick algorithm, or the like. Further, a rotation matrix is generated based on the quaternion, acceleration data in a body coordinate system is converted into acceleration data in a geodetic coordinate system by using the rotation matrix, and gravity acceleration is eliminated. Then, a relative position motion speed is obtained through integration. The speed amplitude of the wrist-worn device can be calculated based on a motion speed in each axial direction.

For another example, after time integration is performed on angular velocities on the x-axis, the y-axis, and the z-axis from the IMU in the first motion data of the wrist-worn device, an angle in which the wrist-worn device rotates around the x-axis, an angle in which the wrist-worn device rotates around the y-axis, and an angle in which the wrist-worn device rotates around the z-axis are obtained.

Specifically, a smartwatch reads the angular velocities on the x-axis, the y-axis, and the z-axis from the real-time angular velocity meter, and performs time integration on the angular velocities read in real time, to obtain the rotation angle of each axis. The smartwatch also reads acceleration on the x-axis, the y-axis, and the z-axis from the real-time accelerometer, and performs time synchronization on the acceleration and the angular velocities (for example, completes time synchronization in an interpolation method). Further, the quaternion is continuously calculated and updated based on the synchronized angular velocities and acceleration data. Posture data (a pitch angle and a roll angle) of the smartwatch relative to the horizontal plane may be obtained through calculation based on the quaternion. The position motion data of the smart device may be obtained through calculation based on the quaternion and the acceleration, for example, an average value of the included angles between the motion directions and the zenith direction, the standard variance of the components of the motion direction on the axes of an on-board east-north-up (ENU) coordinate system, and an average motion speed amplitude.

Further, the smartwatch may also read output from a magnetometer for continuously calculating and updating the quaternion.

Another manner may also be used, and this is not specifically limited in this solution.

Based on data obtained through the foregoing processing, when the posture data and the motion data meet the following condition, it is identified that the wrist-worn device changes from the first posture to the second posture:

when an average pitch angle and/or an average roll angle of the wrist-worn device in the first posture fall/falls within a first preset range;

when an average pitch angle and/or an average roll angle of the wrist-worn device in the second posture fall/falls within a second preset range; and when the included angle between the motion direction of the wrist-worn device and the zenith direction falls within a third preset range or the standard variance of the included angles between the motion direction of the wrist-worn device and the axes of the on-board east-north-up coordinate system is not greater than a first preset variance, the speed amplitude of the wrist-worn device falls within a fourth preset range, and at least one of the angle in which the wrist-worn device rotates around the x-axis, the angle in which the wrist-worn device rotates around the y-axis, and the angle in which the wrist-worn device rotates around the z-axis falls within a fifth preset range, it is identified that the wrist-worn device changes from the first posture to the second posture.

The first motion data may be collected in real time. After collecting the first motion data within preset time, the wrist-worn device obtains, based on the first motion data, that the wrist-worn device changes from the first posture to the second posture. For example, after collecting the first motion data within the preset time, the wrist-worn device first detects that the wrist-worn device is in the first posture at first time, and then detects that the wrist-worn device changes from the first posture to the second posture at second time. Certainly, it may alternatively be that after detecting that the wrist-worn device is in the second posture, the wrist-worn device processes the collected first motion data to detect that the wrist-worn device is in the first posture at first time, and determines that the wrist-worn device changes from the first posture to the second posture; and the like.

Alternatively, with continuous collection of the first motion data, the wrist-worn device detects in real time that the wrist-worn device is in the first posture, and then with continuous collection of the first motion data, the wrist-worn device detects that the wrist-worn device is in the second posture. Certainly, it may alternatively be that after detecting that the wrist-worn device is in the second posture, the wrist-worn device processes the collected first motion data to detect whether the wrist-worn device changes from the first posture to the second posture; or the like. A specific processing manner in which the wrist-worn device identifies the change from the first posture to the second posture is not strictly limited in this solution.

Manner 2:

Generate a quaternion sequence and further generate a relative position motion speed sequence in a geodetic coordinate system based on the first motion data; and input the quaternion sequence and the relative position motion speed sequence into a machine learning algorithm to perform feature extraction and predict whether the wrist-worn device moves to the ear of the user, that is, whether to be the posture in which the hand of the user wearing the wrist-worn device is close to the ear of the user, or whether the wrist-worn device is in the natural reading posture, or the like; and determine that the wrist-worn device changes from the first posture to the second posture.

For example, a quaternion is generated based on angular velocity data and acceleration data by using a Mahony algorithm, a Madgwick algorithm, or the like. Further, a rotation matrix is generated based on the quaternion, the acceleration data in a body coordinate system is converted into acceleration data in the geodetic coordinate system by using the rotation matrix, and gravity acceleration is eliminated. Then, a relative position motion speed is obtained through integration.

The extracted feature may include an average value, a variance, an empirical cumulative distribution function percentile, and the like.

Specifically, a curve in which the foregoing parameters change over time is obtained based on the extracted feature. Based on similarity between the curve and a preset curve, whether the wrist-worn device moves to the ear of the user and whether the wrist-worn device is in the natural reading posture may be determined, and that the wrist-worn device changes from the first posture to the second posture is determined.

The foregoing is merely an example, another manner may also be used, and this is not specifically limited in this solution.

The manners of identifying that the wrist-worn device changes from the first posture to the second posture are described above. Possible implementations in a process in which the wrist-worn device changes from the first posture to the second posture are described below.

In a possible implementation, in the process of changing from the first posture to the second posture, the wrist-worn device may rotate around the ear to move to the ear. Optionally, before the wrist-worn device changes to the second posture, the first motion data of the wrist-worn device meets the following condition: When the wrist-worn device is in the first posture (the current natural reading posture of the user), in a second time interval, a sum of reciprocating rotation angles around the x-axis exceeds a first preset threshold, a sum of reciprocating rotation angles around the y-axis exceeds a second preset threshold, or a sum of reciprocating rotation angles around the z-axis exceeds a third preset threshold. Then, the wrist-worn device moves to the ear. Optionally, the x-axis is located in a direction in which the center of the wrist-worn device points to 3 o'clock, the y-axis is located in a direction in which the center of the wrist-worn device points to 12 o'clock, and the z-axis is perpendicular to the plane on which the wrist-worn device is located and points to above the plane.

In other words, in this example, if the wrist-worn device meets the condition for changing from the first posture to the second posture and the condition for the rotation angle, it indicates that the wrist-worn device changes from the first posture to the second posture, and in the process of changing to the second posture, rotates around the ear and then moves to the ear.

In another possible implementation, after changing from the first posture to the second posture, the wrist-worn device may rotate around the ear to move to the ear. Optionally, when the wrist-worn device is in the second posture (close to the ear of the user), in a third time interval, a sum of reciprocating rotation angles around the x-axis exceeds a fourth preset threshold, a sum of reciprocating rotation angles around the y-axis exceeds a fifth preset threshold, or a sum of reciprocating rotation angles around the z-axis exceeds a sixth preset threshold. Optionally, the x-axis is located in a direction in which the center of the wrist-worn device points to 3 o'clock, the y-axis is located in a direction in which the center of the wrist-worn device points to 12 o'clock, and the z-axis is perpendicular to the plane on which the wrist-worn device is located and points to above the plane.

In other words, in this example, if the wrist-worn device meets the condition for changing from the first posture to the second posture and the condition for the rotation angle, it indicates that the wrist-worn device changes from the first posture to the second posture, and after changing to the second posture, rotates around the ear and then moves to the ear.

Several common man-machine interaction gestures in embodiments of this application are described below.

Example 1: The wrist-worn device changes from the first posture to the second posture. The second posture is the posture in which the hand of the user wearing the wrist-worn device is close to the ear of the user, where the wrist-worn device is close to an ear on an opposite side of the hand of the user wearing the wrist-worn device, and a forearm of the hand of the user wearing the wrist-worn device points upward. That is, the user performs the gesture shown in FIG. 2c.

For example, if the first motion data of the wrist-worn device meets the following condition, it indicates that the user performs the gesture shown in FIG. 2c:

when the wrist-worn device is in the current natural reading posture, in a preset time interval, an average pitch angle ranges from −30 degrees to 110 degrees and a standard variance is less than 12, and an average roll angle ranges from −65 degrees to 65 degrees and a standard variance is less than 12;

when the wrist-worn device is in the posture of moving to the ear, in a fifth time interval, an average pitch angle ranges from 2 degrees to 45 degrees and a standard variance is less than 9, and an average roll angle ranges from 10 degrees to 100 degrees and a standard variance is less than 9;

the average speed amplitude ranges from 0.18 m/s to 7.8 m/s;

the included angle between the motion direction of the wrist-worn device and the zenith direction ranges from 40 degrees to 160 degrees;

the standard variance of the components of the motion direction of the wrist-worn device on the axes of an on-board east-north-up coordinate system is less than 80 degrees; and the angle in which the wrist-worn device rotates around the x-axis ranges from −45 degrees to 75 degrees, the angle in which the wrist-worn device rotates around the y-axis ranges from −40 degrees to 100 degrees, and the angle in which the wrist-worn device rotates around the z-axis ranges from 0 degrees to 128 degrees.

The average speed amplitude and the standard variance of the components of the motion direction of the wrist-worn device on the axes of an on-board east-north-up coordinate system are fused by using a weight of 0.25 to obtain a position motion mode confidence calculation; and the angle in which the wrist-worn device rotates around the x-axis, the angle in which the wrist-worn device rotates around the y-axis, and the angle in which the wrist-worn device rotates around the z-axis are fused by using weights of 0.2, 0.5, and 0.3 or weights of 0.1, 0.45, and 0.45 respectively to obtain a posture motion mode confidence through calculation. The position motion mode confidence and the posture motion mode confidence that are obtained through calculation are weighted by using 0.4 and 0.6 respectively for adding to obtain a result, and the result is compared with a threshold. For example, if a threshold is 0.82, and an addition result is greater than 0.82, it indicates that the user performs the gesture shown in FIG. 2c.

Optionally, the angle in which the wrist-worn device rotates around the y-axis is a reverse rotation angle of a previous phase plus a forward rotation angle of a subsequent phase. The previous phase and the subsequent phase are distinguished based on a time dimension. This is not specifically limited in this solution. In other words, a rotation angle may be distinguished into a forward rotation angle and a reverse rotation angle based on a positive direction of a coordinate axis.

It should be noted that, in this embodiment, the foregoing weight or data is used as an example for description, and calculation may also be performed by using another number or in another manner. This is not strictly limited in this solution.

Example 2: The wrist-worn device changes from the first posture to the second posture. The second posture is the posture in which the hand of the user wearing the wrist-worn device is close to the ear of the user, where the wrist-worn device is close to an ear on a same side of the hand of the user wearing the wrist-worn device, and a forearm of the hand of the user wearing the wrist-worn device points downward. That is, the user performs the gesture shown in FIG. 2d.

For example, if the first motion data of the wrist-worn device meets the following condition, it indicates that the user performs the gesture shown in FIG. 2d:

when the wrist-worn device is in the current natural reading posture, in a preset time interval, an average pitch angle ranges from −30 degrees to 110 degrees and a standard variance is less than 12, and an average roll angle ranges from −65 degrees to 65 degrees and a standard variance is less than 12;

when the wrist-worn device is in the posture of moving to the ear, in a fifth time interval, an average pitch angle ranges from −95 degrees to 5 degrees and a standard variance is less than 9, and an average roll angle ranges from −75 degrees to 15 degrees and a standard variance is less than 9;

the average speed amplitude ranges from 0.18 m/s to 7.8 m/s;

the included angle between the motion direction of the wrist-worn device and the zenith direction ranges from 40 degrees to 160 degrees;

the standard variance of the components of the motion direction of the wrist-worn device on the axes of an on-board east-north-up coordinate system is less than 80 degrees; and the angle in which the wrist-worn device rotates around the x-axis ranges from −24 degrees to 148 degrees, the angle in which the wrist-worn device rotates around the y-axis ranges from −18 degrees to 144 degrees, and the angle in which the wrist-worn device rotates around the z-axis ranges from 15 degrees to 144 degrees.

The average speed amplitude and the standard variance of the components of the motion direction of the wrist-worn device on the axes of an on-board east-north-up coordinate system are fused by using a weight of 0.25 to obtain a position motion mode confidence calculation; and the angle in which the wrist-worn device rotates around the x-axis, the angle in which the wrist-worn device rotates around the y-axis, and the angle in which the wrist-worn device rotates around the z-axis are fused by using weights of 0.2, 0.5, and 0.3 or weights of 0.1, 0.45, and 0.45 respectively to obtain a posture motion mode confidence through calculation. The position motion mode confidence and the posture motion mode confidence that are obtained through calculation are weighted by using 0.4 and 0.6 respectively for adding to obtain a result, and the result is compared with a threshold. For example, if a threshold is 0.82, and an addition result is greater than 0.82, it indicates that the user performs the gesture shown in FIG. 2d.

Optionally, the angle in which the wrist-worn device rotates around the y-axis is a reverse rotation angle of a previous phase plus a forward rotation angle of a subsequent phase. The previous phase and the subsequent phase are distinguished based on a time dimension. This is not specifically limited in this solution. In other words, a rotation angle may be distinguished into a forward rotation angle and a reverse rotation angle based on a positive direction of a coordinate axis.

It should be noted that, in this embodiment, the foregoing weight or data is used as an example for description, and calculation may also be performed by using another number or in another manner. This is not strictly limited in this solution.

The foregoing uses two common gestures as examples for description. For determining performed when the second posture of the wrist-worn device is the posture in which the hand of the user wearing the wrist-worn device is close to the ear of the user, where the wrist-worn device is close to an ear on a same side of the hand of the user wearing the wrist-worn device, and a forearm of the hand of the user wearing the wrist-worn device points upward (that is, the user performs the gesture shown in FIG. 2b), refer to the descriptions of the foregoing examples. Details are not described herein again.

In embodiments of this solution, only a detection method by using the IMU sensor is used for description, and another sensor may also be used for obtaining, for example, a camera or a proximity sensor (an ultrasonic sensor, an infrared sensor, or a capacitive sensor).

In a possible implementation, the method further includes the following step:

collect environmental illumination data of the wrist-worn device.

For example, data collection may be performed based on a four-channel or two-channel environment optical sensor.

Accordingly, step 202 may include the following step:

identify, based on the first motion data of the wrist-worn device and the environmental illumination data of the wrist-worn device, that the wrist-worn device changes from the first posture to the second posture, and the wrist-worn device plays the media information, where the second posture is the posture in which the hand of the user wearing the wrist-worn device is close to ear of the user, the media information is the at least one of the speech message, the text message, and the incoming call information that are received by the wrist-worn device, and the information displayed by the wrist-worn device.

For example, calculate an illumination reduction multiple and/or an illumination reduction value of the wrist-worn device within preset time based on the environmental illumination data; and identify, based on the first motion data of the wrist-worn device and the illumination reduction multiple and/or the illumination reduction value of the wrist-worn device within the preset time, that the wrist-worn device changes from the first posture to the second posture.

Optionally, calculate an average illumination value of the wrist-worn device in a first time period and an average illumination value of the wrist-worn device in a second time period, and then obtain a reduction multiple and a reduction value of previous illumination and later illumination through calculation; and then, identify, based on the illumination reduction multiple, the illumination reduction value, the posture data, and the motion data, that the wrist-worn device changes from the first posture to the second posture.

For example, obtain the posture data and the motion data based on the angular velocity information and the acceleration information of the wrist-worn device; calculate the reduction multiple and the reduction value of previous illumination and later illumination based on the environmental illumination data; and identify, based on the foregoing illumination reduction data, the posture data, and the motion data, that the wrist-worn device changes from the first posture to the second posture.

For an implementation of identifying, based on the first motion data of the wrist-worn device, that the wrist-worn device changes from the first posture to the second posture, refer to the foregoing descriptions. Details are not described herein again.

It is identified, based on a combination of the collected environmental illumination data and the first motion data of the wrist-worn device, that the wrist-worn device changes from the first posture to the second posture. This comprehensively determines a posture change of the wrist-worn device from a plurality of dimensions, has more accurate control, and improves user experience.

The possible implementations in which the wrist-worn device changes from the first posture to the second posture are described above. Possible implementations in which the wrist-worn device plays the media information are described below.

In a possible implementation, the wrist-worn device may determine, based on the received media information, to-be-played audio.

The to-be-played audio may be the speech message, or may be audio converted from a message text by using a text-to-speech (TTS) technology, or the like.

Optionally, before playing the media information, the wrist-worn device converts text information such as the text message and the information displayed by the wrist-worn device into a speech message, and then plays the speech message.

For example, that current time is 15 o'clock is displayed on the wrist-worn device. In this case, the wrist-worn device may convert the displayed time information into a speech for broadcasting: "The current moment is 15 o'clock".

Optionally, the wrist-worn device plays the media information at volume appropriate for ear listening. The volume appropriate for ear listening may be, for example, 30 decibels.

For example, the wrist-worn device is playing a message at high volume, and when detecting changing from the first posture to the second posture, the wrist-worn device plays the message at volume appropriate for ear listening. In this way, the user does not need to manually adjust the volume, which is very convenient and improves user privacy.

In a possible implementation, the wrist-worn device may play the media information via a built-in loudspeaker. Optionally, before playing the media information, the wrist-worn device sends a preset message to a foreground application of the wrist-worn device or an application of the media information, so as to indicate the corresponding application to invoke the loudspeaker of the wrist-worn device to play the media information. For example, the wrist-worn device may send a screen tap event to the application of the media information, so that the application invokes the loudspeaker of the wrist-worn device for playing. The foreground application may be understood as an App or the like that is currently running on the wrist-worn device. This can avoid privacy and social embarrassment problems caused by a speaker mode of the wrist-worn device.

In another possible implementation, the wrist-worn device may further play the media information via a paired headset or the like.

For example, a user wears a headset, and there is a communication connection between the headset and a smartwatch. The headset may be directly connected to the smartwatch in a wireless or wired manner. The smartwatch sends instructions to the headset, so that the headset performs playing.

For another example, a headset is in indirect communication connection to a smartwatch by using a mobile phone. The headset may be connected, in a wireless or wired manner, to another terminal device that is currently paired and connected to the smartwatch, for example, a smartphone. The smartwatch sends instructions to the mobile phone, and a processor in the mobile phone determines the headset connected to the mobile phone, so that the headset performs playing.

According to this embodiment of this application, the wrist-worn device obtains the first motion data of the wrist-worn device, identifies, based on the first motion data of the wrist-worn device, that the wrist-worn device changes from the first posture to the second posture, and plays the media information. This means is used. Compared with the conventional technology in which a wrist-worn device is touched and tapped by a hand to implement control, this solution is more natural and easier to learn, has higher control efficiency, frees two hands of the user, and further improves user experience.

FIG. 3a is another schematic flowchart of a wrist-worn device control method according to an embodiment of this application. As shown in FIG. 3a, the method may include steps 301 to 305. It should be understood that, for ease of description, this application is described in a sequence of 301 to 305. This is not intended to limit all the foregoing steps being definitely performed in the sequence. An execution sequence, an execution time point, a quantity of execution times, and the like of the foregoing one or more steps are not limited in embodiments of this application. An example in which steps 301 to 305 in the wrist-worn device control method are performed by a wrist-worn device is used below for description. This application is also applicable to another execution body. Steps 301 to 305 are specifically as follows.

301: Collect first motion data of the wrist-worn device when detecting that a foreground application status of the wrist-worn device is a target state, where the first motion data includes angular velocity information and acceleration information of the wrist-worn device.

Figure 3C:
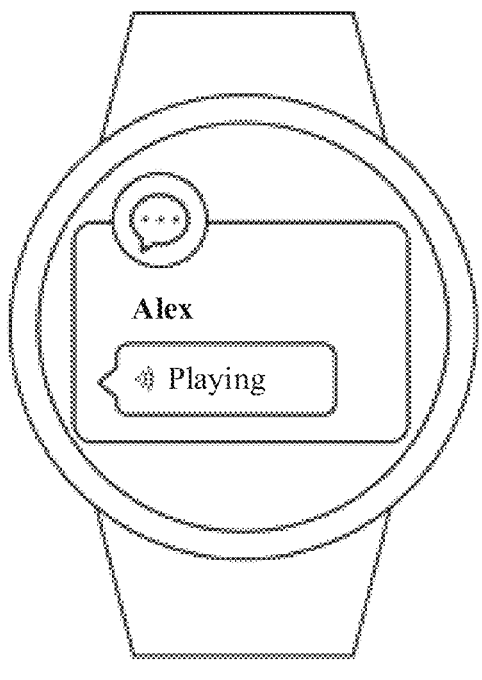
FIG. 3c is a diagram of a wrist-worn device that is playing a message according to an embodiment of this application.
Figure 3D:
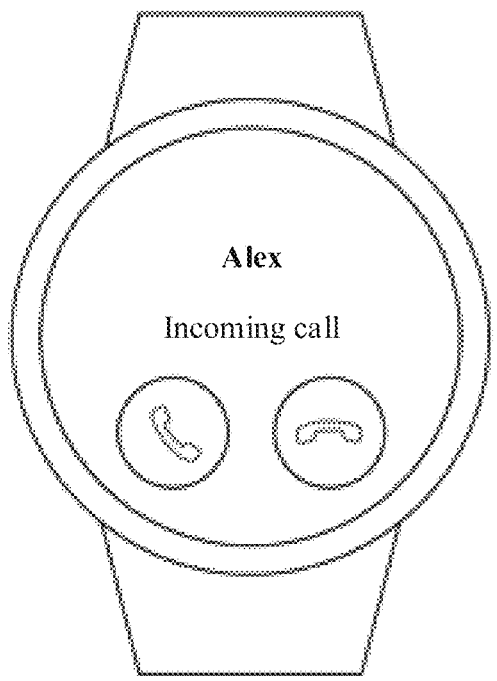
FIG. 3d is a diagram of a wrist-worn device that has received an incoming call according to an embodiment of this application.
Figure 3E:
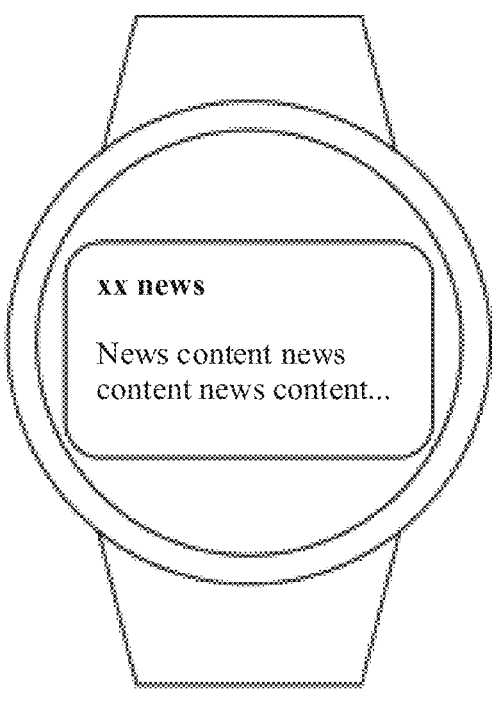
FIG. 3e is a diagram of a wrist-worn device that has received a message according to an embodiment of this application.
Figure 3F:
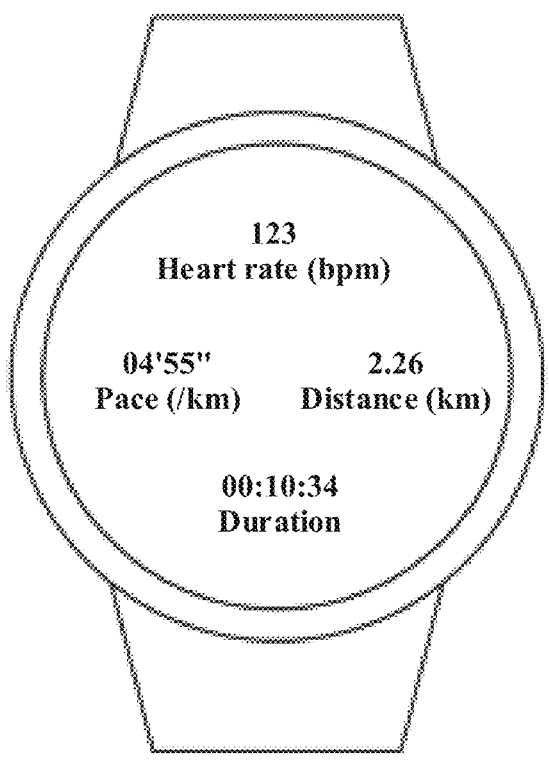
FIG. 3f is a diagram of a wrist-worn device in a motion status monitoring view according to an embodiment of this application.

For example, the target state may be one or more of the following: A display interface of the wrist-worn device displays a message preview view, or the wrist-worn device is playing a message, or the wrist-worn device receives an incoming call and/or a message, or a display interface of the wrist-worn device displays a motion status monitoring view, the wrist-worn device vibrates and/or a screen turns on, or the like.

a1: The display interface of the wrist-worn device displays the message preview view. FIG. 3b is a diagram of message preview. The message preview view includes new speech message received by the wrist-worn device. In other words, when receiving the new message, the wrist-worn device may collect the first motion data, so that when identifying that the wrist-worn device changes from a first posture to a second posture, the wrist-worn device plays the new speech message, or sequentially plays unread messages. In this way, a user can listen to the new message without tapping a screen to perform an operation, which is very convenient, and user experience is good.

a2: The wrist-worn device is playing the message. FIG. 3c is a diagram of message playing. The message playing may be playing a message in a speaker mode of the wrist-worn device, or the like. For example, the wrist-worn device plays the message at high volume, or the wrist-worn device plays the message at low volume. Certainly, the wrist-worn device may further play the message at any volume. In other words, when playing the message, the wrist-worn device may collect the first motion data, so that when identifying that the wrist-worn device changes from a first posture to a second posture, the wrist-worn device plays the playing message. In this way, a user can adjust playing volume without tapping a screen to perform an operation. In addition, user privacy is protected, and user experience is good.

a3: The wrist-worn device receives the incoming call. FIG. 3d is a diagram of an incoming call. When receiving the incoming call, the wrist-worn device may collect the first motion data, so that when identifying that the wrist-worn device changes from a first posture to a second posture, the wrist-worn device plays the received incoming call. It should be noted that playing the received incoming call is answering the incoming call. In this way, a user can answer the incoming call without tapping a screen to perform an operation, which improves convenience of the user.

a4: The wrist-worn device receives the message. The message may be a speech message and a text message. The message may come from a built-in application of an operating system, for example, "Messages", or a third-party instant messaging application like "WeChat" or "QQ". FIG. 3e is a diagram of a message. When receiving a burst new pushed by a news App, local weather pushed by a weather App, or the like, the wrist-worn device may collect the first motion data, so that when identifying that the wrist-worn device changes from a first posture to a second posture, the wrist-worn device plays the received message. In this way, a user can listen to and learn of new information and new messages without tapping a screen to perform an operation, which improves convenience of the user.

a5: The wrist-worn device is in the motion status monitoring view. FIG. 3f is a diagram of motion status monitoring. The view includes motion duration, a pace, a distance, a heart rate, and the like. When being in the motion status monitoring view, the wrist-worn device may collect the first motion data, so that when identifying that the wrist-worn device changes from a first posture to a second posture, the wrist-worn device plays information in the view. In this way, a user can learn of a motion status of the user in real time without tapping a screen to perform an operation, which improves convenience of the user.

a6: The wrist-worn device vibrates and/or the screen turns on. The wrist-worn device vibrates, or the screen turns on, for example, when there is an incoming call, a new message, a reminder, or the like. In this case, collection of the first motion data is triggered, so that when identifying that the wrist-worn device changes from a first posture to a second posture, the wrist-worn device plays corresponding content. This is convenient.

In this embodiment, an operation of collecting the first motion data is triggered when the foreground application status of the wrist-worn device is the target state. It should be noted that another trigger condition may alternatively be used. For example, an operation of collecting the first motion data is triggered when a posture of the wrist-worn device is a preset posture. For example, angular velocities of the wrist-worn device on the three axes x, y, and z are read, and angles in which the wrist-worn device rotates on the three axes are calculated based on the angular velocities. If continuous rotation on any axis exceeds a specific threshold, it is determined that the wrist-worn device is in the preset posture (the user turns a wrist), or the like, and the first motion data is collected. This is not strictly limited in this solution.

302: The wrist-worn device displays a target identifier when detecting that the wrist-worn device is in a first posture, to indicate the user to listen to media information by ear.

For example, in a natural reading posture of the wrist-worn device, an ear icon is displayed on an interface of the wrist-worn device to indicate the user to listen to the media information by ear.

The displayed ear icon may be displayed on an interface play button, a text-to-speech button, or a read button of the wrist-worn device, or displayed on an interface edge of the wrist-worn device in a floating manner, or the like.

Such a design is intuitive and eye-catching, and can improve user experience.

In a possible implementation, when the wrist-worn device is in the first posture, the wrist-worn device determines, based on at least one of a motion status of the wrist-worn device and environmental illumination data of the wrist-worn device, to display the target identifier, so as to indicate the user to listen to the media information by ear.

For example, when the motion status of the wrist-worn device is represented as non-intense motion and/or the environmental illumination data is higher than a preset value, the target identifier is displayed. In this case, the user may be busy moving, or the environmental illumination data is high. The target identifier is displayed in such a scenario, which improves user experience.

In a possible implementation, processing is performed based on the first motion data collected in real time to obtain an average pitch angle and an average roll angle. In a fourth time interval, when the average pitch angle ranges from −30 degrees to 110 degrees, the average roll angle ranges from −65 degrees to 65 degrees, and a standard variance is less than 12, it is determined that the wrist-worn device is in the first posture.

303: The wrist-worn device identifies, based on the first motion data of the wrist-worn device, that the wrist-worn device changes from the first posture to the second posture, and plays the media information, where the second posture is a posture in which a hand of the user wearing the wrist-worn device is close to an ear of the user, the media information is at least one of a speech message, a text message, and incoming call information that are received by the wrist-worn device, and information displayed by the wrist-worn device.

For a specific implementation of identifying, based on the first motion data of the wrist-worn device, that the wrist-worn device changes from the first posture to the second posture, refer to the descriptions in the foregoing embodiments. Details are not described herein again.

In a possible implementation, the wrist-worn device may determine, based on the received media information, to-be-played audio.

The to-be-played audio may be the speech message, or may be audio converted from a message text by using a text-to-speech TTS technology, or the like.

For example, a message preview view shown in FIG. 3b includes a new speech message received by the wrist-worn device. When identifying that the wrist-worn device changes from the first posture to the second posture, the wrist-worn device plays the new speech message, or sequentially plays unread messages. In this way, the user can listen to the new message without tapping a screen to perform an operation, which is very convenient, and user experience is good.

For another example, FIG. 3c is a diagram of message playing. When identifying that the wrist-worn device changes from the first posture to the second posture, the wrist-worn device plays the playing message. In this way, the user can adjust playing volume without tapping a screen to perform an operation. In addition, user privacy is protected, and user experience is good.

For still another example, FIG. 3d is a diagram of an incoming call. When identifying that the wrist-worn device changes from the first posture to the second posture, the wrist-worn device answers the incoming call. In this way, the user can answer the incoming call without tapping a screen to perform an operation, which improves convenience of the user.

In a possible implementation, when the media information is the incoming call information received by the wrist-worn device, the method further includes:

When detecting that the wrist-worn device is in a worn state, the wrist-worn device adjusts an incoming call ringing mode to a silent and vibration mode.

In other words, when the user wears the wrist-worn device, incoming call ringing is adjusted to vibration or the like. In this way, user experience is good.

Optionally, when the media information is the incoming call information received by the wrist-worn device, the method further includes:

The wrist-worn device identifies, based on the first motion data and the environmental illumination data of the wrist-worn device, that the wrist-worn device changes from the first posture to the second posture, and ends ringing and enables a call mode.

In this example, when an incoming call is received, ringing may be directly ended to enter a call. This can help the user free two hands, and the user can answer the call without touching and controlling. User experience is good.

For example, FIG. 3e is a diagram of a message. When identifying that the wrist-worn device changes from the first posture to the second posture, the wrist-worn device plays the received message. In this way, the user can listen to and learn of new information and new messages without tapping a screen to perform an operation, which improves convenience of the user.

For another example, FIG. 3f is a diagram of motion status monitoring. When identifying that the wrist-worn device changes from the first posture to the second posture, the wrist-worn device plays information such as a motion duration, a pace, a distance, and a heart rate in the view. In this way, the user can learn of a motion status of the user in real time without tapping a screen to perform an operation, which improves convenience of the user.

304: Obtain second motion data of the wrist-worn device, where the second motion data includes at least one of angular velocity information and acceleration information of the wrist-worn device.

For collection of the second motion data, refer to the foregoing embodiments. Details are not described herein again.

Optionally, the second motion data is collected after the first motion data is collected. For example, collection may be performed at an interval of preset time, or collection may be performed continuously.

Optionally, the second motion data may be the angular velocity information of the wrist-worn device, or the second motion data may be the acceleration information of the wrist-worn device, or the like.

305: After identifying a third posture based on the second motion data of the wrist-worn device, the wrist-worn device adjusts playing volume of the media information, or the wrist-worn device stops playing the media information.

The third posture may be, for example, a natural reading posture of the user, or a natural hanging posture of the wrist-worn device (the user puts down the hand). This is not specifically limited in this solution.

The adjusting the playing volume of a loudspeaker includes turning up the volume, turning down the volume, saving an adjusted volume, and the like.

The identifying the third posture based on the second motion data of the wrist-worn device may be, for example, performing time integration on angular velocity information of the wrist-worn device, to obtain a sum of reciprocating rotation angles of the wrist-worn device around an x-axis in a first time interval, or obtain a sum of reciprocating rotation angles of the wrist-worn device around a y-axis in a first time interval, or obtain a sum of reciprocating rotation angles of the wrist-worn device around a z-axis in a first time interval, or the like; and determining, based on comparison between the sum of the reciprocating rotation angles and a threshold, whether the wrist-worn device is in the third posture.

For example, in the first time interval, if the sum of the reciprocating rotation angles of the wrist-worn device around the x-axis exceeds a threshold 1, the sum of the reciprocating rotation angles of the wrist-worn device around the y-axis exceeds a threshold 2, or the sum of the reciprocating rotation angles of the wrist-worn device around the z-axis exceeds a threshold 3, the wrist-worn device is in the third posture.

For the descriptions of this part, refer to the foregoing embodiments. Details are not described herein again.

In this embodiment of this application, when detecting that the foreground application status of the wrist-worn device is the target status, the wrist-worn device collects the first motion data of the wrist-worn device, identifies, based on the first motion data of the wrist-worn device, that the wrist-worn device changes from the first posture to the second posture, plays the media information, and after identifying the third posture based on the second motion data of the wrist-worn device, adjusts the playing volume of the media information, or stops playing the media information. This means is used. Compared with the conventional technology in which a wrist-worn device is touched and tapped by a hand to implement control, this solution is more natural and easier to learn, has higher control efficiency, frees two hands of the user, and further improves user experience.

An embodiment of this application further provides a wrist-worn device control method, including:

collecting first motion data of a wrist-worn device, where the first motion data includes angular velocity information and acceleration information of the wrist-worn device; and identifying, based on the first motion data of the wrist-worn device, that the wrist-worn device changes from a first posture to a second posture, and playing, by the wrist-worn device, media information at first preset volume, where the media information is at least one of a speech message, a text message, and incoming call information that are received by the wrist-worn device, and information displayed by the wrist-worn device, and the first preset volume is volume for ear listening, where the second posture is a posture in which a hand of a user wearing the wrist-worn device is close to an ear of the user.

The volume for ear listening may be, for example, 30 decibels. This is not specifically limited in this solution.

The first motion data may be collected in real time. After collecting the first motion data within preset time, the wrist-worn device obtains, based on the first motion data, that the wrist-worn device changes from the first posture to the second posture. For example, after collecting the first motion data within the preset time, the wrist-worn device first detects that the wrist-worn device is in the first posture at first time, and then detects that the wrist-worn device changes from the first posture to the second posture at second time. Certainly, it may alternatively be that after detecting that the wrist-worn device is in the second posture, the wrist-worn device processes the collected first motion data to detect that the wrist-worn device is in the first posture at first time, and determines that the wrist-worn device changes from the first posture to the second posture; and the like.

Alternatively, with continuous collection of the first motion data, the wrist-worn device detects in real time that the wrist-worn device is in the first posture, and then with continuous collection of the first motion data, the wrist-worn device detects that the wrist-worn device is in the second posture. Certainly, it may alternatively be that after detecting that the wrist-worn device is in the second posture, the wrist-worn device processes the collected first motion data to detect whether the wrist-worn device changes from the first posture to the second posture; or the like. A specific processing manner in which the wrist-worn device identifies the change from the first posture to the second posture is not strictly limited in this solution.

According to this embodiment of this application, the wrist-worn device obtains the first motion data of the wrist-worn device, identifies, based on the first motion data of the wrist-worn device, that the wrist-worn device changes from the first posture to the second posture, and plays the media information. This means is used. Compared with the conventional technology in which a wrist-worn device is touched and tapped by a hand to implement control, this solution is more natural and easier to learn, has higher control efficiency, frees two hands of the user, and further improves user experience. Playing is performed at the volume for ear listening. This can resolve privacy and social embarrassment problems caused by a speaker mode of the wrist-worn device.

Optionally, if time during which the wrist-worn device is in the first posture is less than a first threshold, the media information is played at second preset volume, where the second preset volume is not lower than the first preset volume; and/or if time during which the wrist-worn device is in the second posture is less than a second threshold, the media information is played at third preset volume, where the third preset volume is not lower than the first preset volume.

That is, when time during which the wrist-worn device is in the first posture is less than a first threshold, the media information is played at a larger sound; or when time during which the wrist-worn device is in the second posture is less than a second threshold, the media information is played at a larger sound.

Optionally, the identifying, based on the first motion data of the wrist-worn device, that the wrist-worn device changes from a first posture to a second posture includes:

obtaining posture data and motion data based on the angular velocity information and the acceleration information of the wrist-worn device, where the posture data of the wrist-worn device includes an average pitch angle and/or an average roll angle of the wrist-worn device, and the motion data of the wrist-worn device includes a speed amplitude of the wrist-worn device, an included angle between a motion direction of the wrist-worn device and a zenith direction or a standard variance of included angles between a motion direction of the wrist-worn device and axes of an on-board east-north-up coordinate system, and at least one of data about rotation of the wrist-worn device around an x-axis, data about rotation of the wrist-worn device around a y-axis, and data about rotation of the wrist-worn device around a z-axis; and identify, based on the posture data and the motion data, that the wrist-worn device changes from the first posture to the second posture.

Optionally, the identifying, based on the posture data and the motion data, that the wrist-worn device changes from the first posture to the second posture includes:

when an average pitch angle and/or an average roll angle of the wrist-worn device in the first posture fall/falls within a first preset range;

when an average pitch angle and/or an average roll angle of the wrist-worn device in the second posture fall/falls within a second preset range; and when the included angle between the motion direction of the wrist-worn device and the zenith direction falls within a third preset range or the standard variance of the included angles between the motion direction of the wrist-worn device and the axes of the on-board east-north-up coordinate system is not greater than a first preset variance, the speed amplitude of the wrist-worn device falls within a fourth preset range, and at least one of an angle in which the wrist-worn device rotates around the x-axis, an angle in which the wrist-worn device rotates around the y-axis, and an angle in which the wrist-worn device rotates around the z-axis falls within a fifth preset range, identifying that the wrist-worn device changes from the first posture to the second posture.

This means can be used to improve interaction efficiency when the user uses the wrist-worn device. The user does not need to occupy the two hands, and this avoids blocking content and reduces learning costs. In addition, in this solution, motion and posture features when the user moves the wrist close to the ear are used. This improves accuracy of posture identification. Further, in this solution, message playing is controlled with an existing sensor IMU in the wrist-worn device. This reduces design and manufacturing costs.

identify, based on the posture data and the motion data, that the wrist-worn device changes from the first posture to the second posture.

In a possible implementation, the detection module 402 is further configured to:

when an average pitch angle and/or an average roll angle of the wrist-worn device in the first posture fall/falls within a first preset range;

when an average pitch angle and/or an average roll angle of the wrist-worn device in the second posture fall/falls within a second preset range; and when the included angle between the motion direction of the wrist-worn device and the zenith direction falls within a third preset range or the standard variance of the included angles between the motion direction of the wrist-worn device and the axes of the on-board east-north-up coordinate system is not greater than a first preset variance, the speed amplitude of the wrist-worn device falls within a fourth preset range, and at least one of the angle in which the wrist-worn device rotates around the x-axis, the angle in which the wrist-worn device rotates around the y-axis, and the angle in which the wrist-worn device rotates around the z-axis falls within a fifth preset range, identify that the wrist-worn device changes from the first posture to the second posture.

In a possible implementation, the collection module 401 is further configured to:

collect environmental illumination data of the wrist-worn device; and the detection module 402 is further configured to:

identify, based on the first motion data and the environmental illumination data of the wrist-worn device, that the wrist-worn device changes from the first posture to the second posture.

In a possible implementation, the detection module 402 is further configured to:

calculate an illumination reduction multiple and/or an illumination reduction value of the wrist-worn device within preset time based on the environmental illumination data; and identify, based on the first motion data of the wrist-worn device and the illumination reduction multiple and/or the illumination reduction value of the wrist-worn device within the preset time, that the wrist-worn device changes from the first posture to the second posture.

In a possible implementation, the detection module 402 is configured to:

generate a quaternion sequence and a relative position motion speed sequence based on the first motion data;

perform feature extraction on the quaternion sequence and the relative position motion speed sequence to obtain an extracted feature; and determine, based on the extracted feature, that the hand of the user wearing the wrist-worn device is close to the ear of the user.

In a possible implementation, the second posture is the posture in which the hand of the user wearing the wrist-worn device is close to the ear of the user, where the wrist-worn device is close to an ear on an opposite side of the hand of the user wearing the wrist-worn device, and a forearm of the hand of the user wearing the wrist-worn device points upward.

In a possible implementation, the second posture is the posture in which the hand of the user wearing the wrist-worn device is close to the ear of the user, where the wrist-worn device is close to an ear on a same side of the hand of the user wearing the wrist-worn device, and a forearm of the hand of the user wearing the wrist-worn device points downward, or a forearm of the hand of the user wearing the wrist-worn device is parallel to a horizontal plane.

In a possible implementation, a watch face of the wrist-worn device faces a human face or the ear.

In a possible implementation, when the wrist-worn device is in the first posture, the wrist-worn device control apparatus displays a target identifier, to indicate the user to listen to the media information by ear.

In a possible implementation, when the wrist-worn device is in the first posture, the wrist-worn device control apparatus determines, based on at least one of a motion status of the wrist-worn device and the environmental illumination data of the wrist-worn device, to display the target identifier, so as to indicate the user to listen to the media information by ear.

In a possible implementation, when identifying, based on the first motion data of the wrist-worn device, that the wrist-worn device changes from the first posture to the second posture, the wrist-worn device control apparatus shields a touch control function, a knob function, or a button function of the wrist-worn device.

In a possible implementation, when the media information is the incoming call information received by the wrist-worn device, the playing module 403 is further configured to:

when it is detected that the wrist-worn device is in a worn state, adjust an incoming call ringing mode to a silent and vibration mode.

In a possible implementation, when the media information is the incoming call information received by the wrist-worn device, the playing module 403 is further configured to:

identify, based on the first motion data and the environmental illumination data of the wrist-worn device, that the wrist-worn device changes from the first posture to the second posture, end ringing, and enable a call mode.

In a possible implementation, before the wrist-worn device plays the media information, the apparatus further includes a sending module, configured to:

send a preset message to a foreground application of the wrist-worn device or an application of the media information, to indicate the application to invoke a loudspeaker of the wrist-worn device to play the media information.

In a possible implementation, the collection module 401 is further configured to:

obtain second motion data of the wrist-worn device, where the second motion data includes at least one of angular velocity information and acceleration information of the wrist-worn device;

the detection module 402 is further configured to identify a third posture based on the second motion data of the wrist-worn device; and the playing module 403 is further configured to: adjust playing volume of the media information, or stop playing the media information.

In a possible implementation, the collection module 401 is triggered to collect the first motion data of the wrist-worn device when the detection module 402 detects that a foreground application status of the wrist-worn device is at least one of the following:

a display interface of the wrist-worn device displays a message preview view, or the wrist-worn device is playing a message, or the wrist-worn device receives an incoming call and/or a message, or a display interface of the wrist-worn device displays a motion status monitoring view, or the wrist-worn device vibrates and/or a screen turns on.

In a possible implementation, the first posture is a posture in which the user reads on the screen.

In a possible implementation, the playing module 403 is configured to play the media information at preset volume, where the preset volume is volume for ear listening.

According to this embodiment of this application, the wrist-worn device control apparatus obtains the first motion data of the wrist-worn device, identifies, based on the first motion data of the wrist-worn device, that the wrist-worn device changes from the first posture to the second posture, and plays the media information. This means is used. Compared with the conventional technology in which a wrist-worn device is touched and tapped by a hand to implement control, this solution is more natural and easier to learn, has higher control efficiency, frees two hands of the user, and further improves user experience.

For the descriptions of the foregoing modules, refer to the foregoing embodiments. Details are not described herein again.

An embodiment of this application further provides a wrist-worn device control apparatus. The wrist-worn device control apparatus is configured to implement the foregoing wrist-worn device control method.

The wrist-worn device control apparatus may include a collection module, a detection module, and a playing module, which are specifically described in the following.

The collection module is configured to collect first motion data of a wrist-worn device, where the first motion data includes angular velocity information and acceleration information of the wrist-worn device.

The detection module is configured to identify, based on the first motion data of the wrist-worn device, that the wrist-worn device changes from a first posture to a second posture, where the second posture is a posture in which a hand of a user wearing the wrist-worn device is close to an ear of the user.

The playing module is configured to play media information at first preset volume, where the media information is at least one of a speech message, a text message, and incoming call information that are received by the wrist-worn device, and information displayed by the wrist-worn device, and the first preset volume is volume for ear listening.

Optionally, if time during which the wrist-worn device is in the first posture is less than a first threshold, the playing module is configured to play the media information at second preset volume, where the second preset volume is not lower than the first preset volume; and/or if time during which the wrist-worn device is in the second posture is less than a second threshold, the playing module is configured to play the media information at third preset volume, where the third preset volume is not lower than the first preset volume.

Optionally, the detection module is configured to:

obtain posture data and motion data based on the angular velocity information and the acceleration information of the wrist-worn device, where the posture data of the wrist-worn device includes an average pitch angle and/or an average roll angle of the wrist-worn device, and the motion data of the wrist-worn device includes a speed amplitude of the wrist-worn device, an included angle between a motion direction of the wrist-worn device and a zenith direction or a standard variance of included angles between a motion direction of the wrist-worn device and axes of an on-board east-north-up coordinate system, and at least one of data about rotation of the wrist-worn device around an x-axis, data about rotation of the wrist-worn device around a y-axis, and data about rotation of the wrist-worn device around a z-axis; and identify, based on the posture data and the motion data, that the wrist-worn device changes from the first posture to the second posture.

Optionally, the detection module is further configured to:

when an average pitch angle and/or an average roll angle of the wrist-worn device in the first posture fall/falls within a first preset range;

when an average pitch angle and/or an average roll angle of the wrist-worn device in the second posture fall/falls within a second preset range; and when the included angle between the motion direction of the wrist-worn device and the zenith direction falls within a third preset range or the standard variance of the included angles between the motion direction of the wrist-worn device and the axes of the on-board east-north-up coordinate system is not greater than a first preset variance, the speed amplitude of the wrist-worn device falls within a fourth preset range, and at least one of the angle in which the wrist-worn device rotates around the x-axis, the angle in which the wrist-worn device rotates around the y-axis, and the angle in which the wrist-worn device rotates around the z-axis falls within a fifth preset range, identify that the wrist-worn device changes from the first posture to the second posture.

In a possible implementation, the detection module is configured to:

generate a quaternion sequence and a relative position motion speed sequence based on the first motion data;

perform feature extraction on the quaternion sequence and the relative position motion speed sequence to obtain an extracted feature; and determine, based on the extracted feature, that the hand of the user wearing the wrist-worn device is close to the ear of the user.

In a possible implementation, the second posture is the posture in which the hand of the user wearing the wrist-worn device is close to the ear of the user, where the wrist-worn device is close to an ear on an opposite side of the hand of the user wearing the wrist-worn device, and a forearm of the hand of the user wearing the wrist-worn device points upward.

In a possible implementation, the second posture is the posture in which the hand of the user wearing the wrist-worn device is close to the ear of the user, where the wrist-worn device is close to an ear on a same side of the hand of the user wearing the wrist-worn device, and a forearm of the hand of the user wearing the wrist-worn device points downward, or a forearm of the hand of the user wearing the wrist-worn device is parallel to a horizontal plane.

In a possible implementation, a watch face of the wrist-worn device faces a human face or the ear.

In a possible implementation, when the wrist-worn device is in the first posture, the wrist-worn device control apparatus displays a target identifier, to indicate the user to listen to the media information by ear.

In a possible implementation, when identifying, based on the first motion data of the wrist-worn device, that the wrist-worn device changes from the first posture to the second posture, the wrist-worn device control apparatus shields a touch control function, a knob function, or a button function of the wrist-worn device.

In a possible implementation, before the wrist-worn device plays the media information, the apparatus further includes a sending module, configured to:

send a preset message to a foreground application of the wrist-worn device or an application of the media information, to indicate the application to invoke a loudspeaker of the wrist-worn device to play the media information.

In a possible implementation, the collection module is further configured to:

collect environmental illumination data of the wrist-worn device; and the detection module is further configured to:

identify, based on the first motion data and the environmental illumination data of the wrist-worn device, that the wrist-worn device changes from the first posture to the second posture.

In a possible implementation, the collection module is further configured to:

obtain second motion data of the wrist-worn device, where the second motion data includes at least one of angular velocity information and acceleration information of the wrist-worn device;

the detection module is further configured to identify a third posture based on the second motion data of the wrist-worn device; and the playing module is further configured to: adjust playing volume of the media information, or stop playing the media information.

In a possible implementation, the collection module is triggered to collect the first motion data of the wrist-worn device when the detection module detects that a foreground application status of the wrist-worn device is at least one of the following:

a display interface of the wrist-worn device displays a message preview view, or the wrist-worn device is playing a message, or the wrist-worn device receives an incoming call and/or a message, or a display interface of the wrist-worn device displays a motion status monitoring view, or the wrist-worn device vibrates and/or a screen turns on.

In a possible implementation, the first posture is a posture in which the user reads on the screen.

For the descriptions of the foregoing modules, refer to the foregoing embodiments. Details are not described herein again.

In embodiments, the wrist-worn device is presented in a form of a module. The "module" herein may be an application-specific integrated circuit (ASIC), a processor for executing one or more software or firmware programs, a memory, an integrated logic circuit, and/or another component that may provide the foregoing functions.

Figure 4:
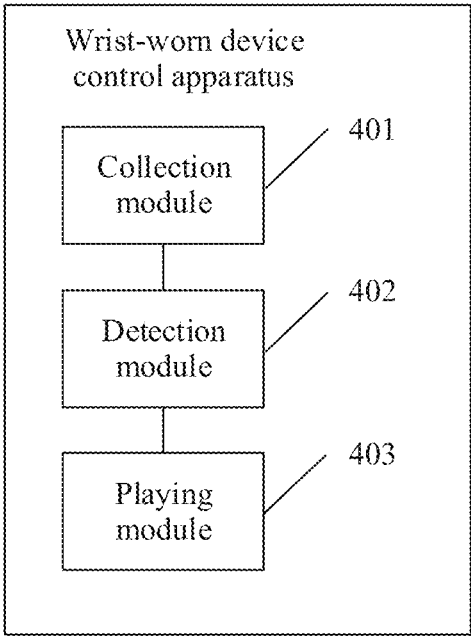
FIG. 4 is a diagram of a structure of a wrist-worn device control apparatus according to an embodiment of this application.
Figure 5:
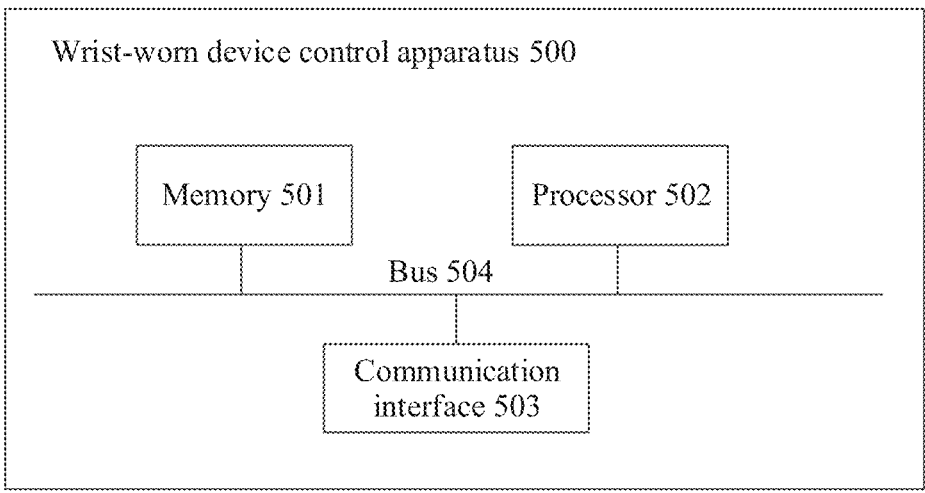
FIG. 5 is a diagram of a structure of another wrist-worn device control apparatus according to an embodiment of this application.

In addition, the collection module 401, the detection module 402, and the playing module 403 shown in FIG. 4, and the collection module, the detection module, and the playing module included in the another wrist-worn device control apparatus in the solutions, all may be implemented by using a processor 502 in a wrist-worn device control apparatus shown in FIG. 5.

FIG. 5 is a diagram of a hardware structure of the wrist-worn device control apparatus according to an embodiment of this application. The wrist-worn device control apparatus 500 (the apparatus 500 may be a computer device) shown in FIG. 5 includes a memory 501, a processor 502, a communication interface 503, and a bus 504. The memory 501, the processor 502, and the communication interface 503 are communicatively connected to each other through the bus 504.

The memory 501 may be a read-only memory (ROM), a static storage device, a dynamic storage device, or a random access memory (RAM).

The memory 501 may store a program. When the program stored in the memory 501 is executed by the processor 502, the processor 502 and the communication interface 503 are configured to perform steps of the wrist-worn device control method in embodiments of this application.

The processor 502 may be a general-purpose central processing unit (CPU), a microprocessor, an application-specific integrated circuit (ASIC), a graphics processing unit (GPU), or one or more integrated circuits, and is configured to execute a related program, to implement a function that needs to be performed by a unit in the wrist-worn device control apparatus in embodiments of this application, or perform the wrist-worn device control method in method embodiments of this application.

Alternatively, the processor 502 may be an integrated circuit chip and has a signal processing capability. In an implementation process, the steps of the wrist-worn device control method in this application may be completed by using a hardware integrated logic circuit or instructions in a form of software in the processor 502. The processor 502 may be a general-purpose processor, a digital signal processor (DSP), an application-specific integrated circuit (ASIC), a field programmable gate array (FPGA) or another programmable logic device, a discrete gate or transistor logic device, or a discrete hardware component. The processor may implement or perform the methods, the steps, and logical block diagrams that are disclosed in embodiments of this application. The general-purpose processor may be a microprocessor, or the processor may be any conventional processor, or the like. Steps of the methods disclosed with reference to embodiments of this application may be directly executed and accomplished by using a hardware decoding processor, or may be executed and accomplished by using a combination of hardware and software modules in the decoding processor. A software module may be located in a mature storage medium in the art, like a random access memory, a flash memory, a read-only memory, a programmable read-only memory, an electrically erasable programmable memory, or a register. The storage medium is located in the memory 501. The processor 502 reads information in the memory 501, and completes, in combination with hardware of the processor, a function that needs to be performed by the unit included in the wrist-worn device control apparatus in embodiments of this application, or performs the wrist-worn device control method in method embodiments of this application.

The communication interface 503 uses a transceiver apparatus, for example but not limitation, a transceiver, to implement communication between the apparatus 500 and another device or a communication network. For example, data may be obtained through the communication interface 503.

The bus 504 may include a channel for transmitting information between components (for example, the memory 501, the processor 502, and the communication interface 503) in the apparatus 500.

It should be noted that although the apparatus 500 shown in FIG. 5 only shows the memory, the processor, and the communication interface, in a specific implementation process, a person skilled in the art should understand that the apparatus 500 further includes other components that are necessary to implement normal running. In addition, according to a specific requirement, a person skilled in the art should understand that the apparatus 500 may further include hardware components for implementing other additional functions. In addition, a person skilled in the art should understand that the apparatus 500 may include only components for implementing embodiments of this application, but not necessarily include all the components shown in FIG. 5.

An embodiment of this application further provides a computer-readable storage medium. The computer-readable storage medium stores instructions. When the instructions are run on a computer or a processor, the computer or the processor is enabled to perform one or more steps in any one of the foregoing methods.

An embodiment of this application further provides a computer program product including instructions. When the computer program product runs on a computer or a processor, the computer or the processor is enabled to perform one or more steps in any one of the foregoing methods.

It may be clearly understood by a person skilled in the art that, for the purpose of convenient and brief description, for a detailed working process of the foregoing system, apparatus, and unit, refer to the specific description of a corresponding step process in the foregoing method embodiments. Details are not described herein again.

It should be understood that unless otherwise specified, "/" in descriptions of this application indicates an "or" relationship between associated objects. For example, A/B may indicate A or B. A and B may be singular or plural. In addition, in the descriptions of this application, "a plurality of" means two or more than two unless otherwise specified. "At least one of the following items (pieces)" or a similar expression thereof refers to any combination of these items, including any combination of singular items (pieces) or plural items (pieces). For example, at least one item (piece) of a, b, or c may indicate: a, b, c, a and b, a and c, b and c, or a, b, and c, where a, b, and c may be singular or plural. In addition, to clearly describe the technical solutions in embodiments of this application, terms such as "first" and "second" are used in embodiments of this application to distinguish between same items or similar items that provide basically same functions or purposes. A person skilled in the art may understand that the terms such as "first" and "second" do not limit a quantity or an execution sequence, and the terms such as "first" and "second" do not indicate a definite difference. In addition, in embodiments of this application, terms such as "example" or "for example" are used to represent giving an example, an illustration, or a description. Any embodiment or design scheme described as an "example" or "for example" in embodiments of this application should not be explained as being more preferred or having more advantages than another embodiment or design scheme. Exactly, use of the terms such as "example" or "for example" is intended to present a related concept in a specific manner for ease of understanding.

In the several embodiments provided in this application, it should be understood that the disclosed system, apparatus, and method may be implemented in other manners. For example, division into the units is merely logical function division and may be another division in actual implementation. For example, a plurality of units or components may be combined or integrated into another system, or some features may be ignored or not performed. The displayed or discussed mutual couplings or direct couplings or communication connections may be implemented through some interfaces. The indirect couplings or communication connections between the apparatuses or units may be implemented in electronic, mechanical, or other forms.

The units described as separate parts may or may not be physically separate, and parts displayed as units may or may not be physical units, in other words, may be located in one position, or may be distributed on a plurality of network units. Some or all of the units may be selected based on actual requirements to achieve the objectives of the solutions in embodiments.

All or some of the foregoing embodiments may be implemented by using software, hardware, firmware, or any combination thereof. When software is used to implement embodiments, all or some of embodiments may be implemented in a form of a computer program product. The computer program product includes one or more computer instructions. When the computer program instructions are loaded and executed on a computer, the procedures or functions according to embodiments of this application are all or partially generated. The computer may be a general-purpose computer, a dedicated computer, a computer network, or other programmable apparatuses. The computer instructions may be stored in a computer-readable storage medium, or transmitted by using the computer-readable storage medium. The computer instructions may be transmitted from a website, computer, server, or data center to another website, computer, server, or data center in a wired (for example, a coaxial cable, an optical fiber, or a digital subscriber line (DSL)) or wireless (for example, infrared, radio, or microwave) manner. The computer-readable storage medium may be any usable medium accessible by the computer, or a data storage device, like a server or a data center that integrates one or more usable media. The usable medium may be a read-only memory (ROM), a random access memory (RAM), or a magnetic medium, for example, a floppy disk, a hard disk, a magnetic tape, a magnetic disk, or an optical medium, for example, a digital versatile disc (DVD), or a semiconductor medium, for example, a solid-state drive (SSD).

The foregoing descriptions are merely specific implementations of embodiments of this application, but are not intended to limit the protection scope of embodiments of this application. Any variation or replacement within the technical scope disclosed in embodiments of this application shall fall within the protection scope of embodiments of this application. Therefore, the protection scope of embodiments of this application shall be subject to the protection scope of the claims.

The invention claimed is:

1. A wrist-worn device control method, comprising:
   collecting first motion data of a wrist-worn device, wherein the first motion data comprises angular velocity information and acceleration information of the wrist-worn device;
   collecting environmental illumination data of the wrist-worn device;
   calculating an illumination reduction multiple and/or an illumination reduction value of the wrist-worn device within preset time based on the environmental illumination data;
   identifying, based on the first motion data of the wrist-worn device and the illumination reduction multiple and/or the illumination reduction value of the wrist-worn device within the preset time, that the wrist-worn device changes from a first posture to a second posture; and
   playing, based on the identification, media information, wherein the media information is at least one of a speech message, a text message, and incoming call information that are received by the wrist-worn device, or information displayed by the wrist-worn device, wherein the second posture is a posture in which a hand of a user wearing the wrist-worn device is close to an ear of the user.

2. The method according to claim 1, wherein the method further comprises:

obtaining posture data and motion data based on the angular velocity information and the acceleration information of the wrist-worn device, wherein the posture data of the wrist-worn device comprises an average pitch angle and/or an average roll angle of the wrist-worn device, and the motion data of the wrist-worn device comprises a speed amplitude of the wrist-worn device, one of an included angle between a motion direction of the wrist-worn device and a zenith direction or a standard variance of included angles between a motion direction of the wrist-worn device and axes of an on-board east-north-up coordinate system, and at least one of data about rotation of the wrist-worn device around an x-axis, data about rotation of the wrist-worn device around a y-axis, or data about rotation of the wrist-worn device around a z-axis; and wherein the identifying is further based on the posture data.

3. The method according to claim 2, wherein the identifying that the wrist-worn device changes from the first posture to the second posture comprises:

when an average pitch angle and/or an average roll angle of the wrist-worn device in the first posture fall/falls within a first preset range;

when an average pitch angle and/or an average roll angle of the wrist-worn device in the second posture fall/falls within a second preset range; and when the included angle between the motion direction of the wrist-worn device and the zenith direction falls within a third preset range or the standard variance of the included angles between the motion direction of the wrist-worn device and the axes of the on-board east-north-up coordinate system is not greater than a first preset variance, the speed amplitude of the wrist-worn device falls within a fourth preset range, and at least one of an angle in which the wrist-worn device rotates around the x-axis, an angle in which the wrist-worn device rotates around the y-axis, or an angle in which the wrist-worn device rotates around the z-axis falls within a fifth preset range, identifying that the wrist-worn device changes from the first posture to the second posture.

4. The method according to claim 1, the method further comprising:

generating a quaternion sequence and a relative position motion speed sequence based on the first motion data;

performing feature extraction on the quaternion sequence and the relative position motion speed sequence to obtain an extracted feature; and determining, based on the extracted feature, that the hand of the user wearing the wrist-worn device is close to the ear of the user.

5. The method according to claim 1, wherein the second posture is the posture in which the hand of the user wearing the wrist-worn device is close to the ear of the user, wherein the wrist-worn device is close to an ear on an opposite side of the hand of the user wearing the wrist-worn device, and a forearm of the hand of the user wearing the wrist-worn device points upward.

6. The method according to claim 5, wherein a watch face of the wrist-worn device faces a human face or the ear.

7. The method according to claim 1, wherein the second posture is the posture in which the hand of the user wearing the wrist-worn device is close to the ear of the user, wherein the wrist-worn device is close to an ear on a same side of the hand of the user wearing the wrist-worn device, and a forearm of the hand of the user wearing the wrist-worn device points downward, or a forearm of the hand of the user wearing the wrist-worn device is parallel to a horizontal plane.

8. The method according to claim 1, wherein when the wrist-worn device is in the first posture, the wrist-worn device determines, based on at least one of a motion status of the wrist-worn device or environmental illumination data of the wrist-worn device, to display a target identifier, so as to indicate the user to listen to the media information by ear.

9. The method according to claim 1, wherein when identifying, based on the first motion data of the wrist-worn device, that the wrist-worn device changes from the first posture to the second posture, the wrist-worn device shields a touch control function, a knob function, or a button function.

10. The method according to claim 1, wherein when the media information is the incoming call information received by the wrist-worn device, the method further comprises:

when detecting that the wrist-worn device is in a worn state, adjusting an incoming call ringing mode to a silent and vibration mode.

11. The method according to claim 1, wherein when the media information is the incoming call information received by the wrist-worn device, the method further comprises:

identifying, based on the first motion data and the environmental illumination data of the wrist-worn device, that the wrist-worn device changes from the first posture to the second posture, and ending ringing and enabling a call mode.

12. The method according to claim 1, wherein before the playing, by the wrist-worn device, media information, the method further comprises:

sending a preset message to a foreground application of the wrist-worn device or an application of the media information, to indicate the application to invoke a loudspeaker of the wrist-worn device to play the media information.

13. The method according to claim 1, the method further comprising:

obtaining second motion data of the wrist-worn device, wherein the second motion data comprises at least one of angular velocity information or acceleration information of the wrist-worn device; and after identifying a third posture based on the second motion data of the wrist-worn device, adjusting, by the wrist-worn device, playing volume of the media information, or stopping, by the wrist-worn device, playing the media information.

14. The method according to claim 1, wherein an operation of collecting the first motion data of the wrist-worn device is triggered when it is detected that a foreground application status of the wrist-worn device is at least one of the following:

a display interface of the wrist-worn device displays a message preview view, the wrist-worn device is playing a message, at least one of the wrist-worn device receives an incoming call or a message, a display interface of the wrist-worn device displays a motion status monitoring view, or at least one of the wrist-worn device vibrates or a screen turns on.

15. The method according to claim 1, wherein the first posture is a posture in which the user reads on the screen.

16. The method according to claim 1, wherein the wrist-worn device plays the media information at preset volume, wherein the preset volume is volume for ear listening.

17. The method according to claim 1, wherein the playing the media information, the method further comprises:

playing the media information at first preset volume that is volume for ear listening.

18. The method according to claim 17, wherein if time during which the wrist-worn device is in the first posture is less than a first threshold, the media information is played at second preset volume, wherein the second preset volume is not lower than the first preset volume; and/or if time during which the wrist-worn device is in the second posture is less than a second threshold, the media information is played at third preset volume, wherein the third preset volume is not lower than the first preset volume.

19. A wrist-worn device control apparatus, comprising a processor and a communication interface, wherein the communication interface is configured to receive and/or send data, and the processor is configured to invoke computer instructions to enable the wrist-worn device control apparatus to perform operations comprising:

collecting first motion data of a wrist-worn device, wherein the first motion data comprises angular velocity information and acceleration information of the wrist-worn device;

collecting environmental illumination data of the wrist-worn device;

calculating an illumination reduction multiple and/or an illumination reduction value of the wrist-worn device within preset time based on the environmental illumination data;

identifying, based on the first motion data of the wrist-worn device and the illumination reduction multiple and/or the illumination reduction value of the wrist-worn device within the preset time, that the wrist-worn device changes from a first posture to a second posture; and playing media information, wherein the media information is at least one of a speech message, a text message, and incoming call information that are received by the wrist-worn device, or information displayed by the wrist-worn device, wherein the second posture is a posture in which a hand of a user wearing the wrist-worn device is close to an ear of the user.

20. A non-transitory computer readable medium which contains computer-executable instructions that, when executed by a processor of a wrist-worn device, enables the wrist-worn device to perform operations comprising:

collecting first motion data of the wrist-worn device, wherein the first motion data comprises angular velocity information and acceleration information of the wrist-worn device;

collecting environmental illumination data of the wrist-worn device;

calculating an illumination reduction multiple and/or an illumination reduction value of the wrist-worn device within preset time based on the environmental illumination data;

identifying, based on the first motion data of the wrist-worn device and the illumination reduction multiple and/or the illumination reduction value of the wrist-worn device within the preset time, that the wrist-worn device changes from a first posture to a second posture; and playing media information, wherein the media information is at least one of a speech message, a text message, and incoming call information that are received by the wrist-worn device, or information displayed by the wrist-worn device, wherein the second posture is a posture in which a hand of a user wearing the wrist-worn device is close to an ear of the user.

* * * * *